(12) United States Patent
Blandino et al.

(10) Patent No.: US 12,114,681 B2
(45) Date of Patent: Oct. 15, 2024

(54) FRAGRANCE AND FLAVOR MATERIALS

(71) Applicant: TAKASAGO INTERNATIONAL CORPORATION, Tokyo (JP)

(72) Inventors: Maureen Blandino, Dumont, NJ (US); Kenji Tanuma, Hiratsuka (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 820 days.

(21) Appl. No.: 15/734,924

(22) PCT Filed: Jun. 4, 2019

(86) PCT No.: PCT/US2019/035441
§ 371 (c)(1),
(2) Date: Dec. 3, 2020

(87) PCT Pub. No.: WO2019/236614
PCT Pub. Date: Dec. 12, 2019

(65) Prior Publication Data
US 2021/0227864 A1 Jul. 29, 2021

Related U.S. Application Data

(60) Provisional application No. 62/680,294, filed on Jun. 4, 2018.

(51) Int. Cl.
*A23L 27/20* (2016.01)
*C11B 9/00* (2006.01)

(52) U.S. Cl.
CPC ....... *A23L 27/2026* (2016.08); *A23L 27/2028* (2016.08); *C11B 9/0015* (2013.01); *C11B 9/0023* (2013.01)

(58) Field of Classification Search
None
See application file for complete search history.

(56) References Cited

U.S. PATENT DOCUMENTS

| 4,128,509 A | 12/1978 | Schleppnik |
| 4,229,600 A | 10/1980 | Kobayashi et al. |
| 2009/0209449 A1* | 8/2009 | Majeed ................. C11B 9/0034 512/22 |
| 2010/0016197 A1* | 1/2010 | Granier ................. C11B 9/0034 510/106 |

FOREIGN PATENT DOCUMENTS

| JP | 2012-106225 A | 6/2012 |
| WO | WO 2011/029895 A2 | 3/2011 |

OTHER PUBLICATIONS

International Search Report mailed Nov. 7, 2019 in International Application No. PCT/US2019/035441.
Miller et al., "Alkene-Directed, Nickel-Catalyzed Alkyne Coupling Reactions," Journal of The American Chemical Society, 126(13):4130-4131 (2004).

* cited by examiner

*Primary Examiner* — Lien T Tran
(74) *Attorney, Agent, or Firm* — Baker Botts L.L.P.

(57) ABSTRACT

The synthesis and application of compounds having unique and desired flavor and/or fragrance characteristics are provided herein. The compounds herein can be employed alone or incorporated as fragrance or flavor ingredients in fragrance or flavor compositions. The application is also directed to consumer products comprising such derivatives and/or fragrance or flavor compositions.

9 Claims, No Drawings

FRAGRANCE AND FLAVOR MATERIALS

CROSS-REFERENCE TO RELATED APPLICATIONS

This application is a U.S. National Stage Patent Application under 35 U.S.C. § 371 of International Patent Application No. PCT/US2019/035441, filed on Jun. 4, 2019, which claims priority to U.S. Provisional Patent Application Ser. No. 62/680,294, filed on Jun. 4, 2018, the contents of each of which are hereby incorporated by reference in their entireties.

FIELD

The present application relates to compounds useful as fragrance or flavor compounds in fragrance or flavor compositions.

BACKGROUND

There is a continuing interest in the preparation of novel fragrance and flavor compounds to provide pleasing organoleptic characteristics in new fragrance and flavor compositions. For a wide variety of consumer products, the decision to purchase the product or not can be based on whether the scent or taste of the product is deemed pleasing by the consumer. Thus, there remains a need and demand for unique fragrance and flavor compositions with pleasing and consumer preferred odor and taste profiles for use in consumer products.

SUMMARY

It is well known in the fragrance and flavor industries that small changes in the chemical structure of a compound can impact organoleptic properties in surprising and unpredictable ways. The present disclosure is directed to the synthesis and application of compounds having unique and desired fragrance and/or flavor characteristics. The compounds of the present disclosure can be employed alone or incorporated into fragrance or flavor compositions.

In certain embodiments the present disclosure provides for fragrance or flavor compounds represented by Formula Ia:

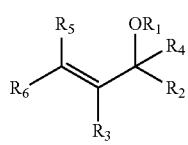

Formula Ia wherein $R_1$ can be H, alkyl or C(O)$R_7$, $R_2$ can be H, alkyl, alkenyl, alkynyl, linear or branched aryl, $R_3$ can be H, alkyl, alkenyl, alkynyl, linear or branched aryl, $R_4$ can be H, alkyl, alkenyl, alkynyl, linear or branched aryl, $R_5$ can be H or alkyl, $R_6$ can be cyclohexyl, cyclohexenyl or bicyclo[2.2.1]hept-5-enyl, $R_7$ can be H, alkyl, alkenyl, alkynyl, linear or branched aryl, and wherein the compound of Formula Ia can be in a form of its racemates, its pure stereoisomers, enantiomers or diastereomers, or in a form of mixtures of stereoisomers, enantiomers or diastereomers, in any mixing ratio.

In particular embodiments, the present disclosure provides for fragrance or flavor compounds represented by Formula Ia, wherein $R_1$ can be H, alkyl or C(O)$R_7$, $R_2$ can be alkyl, alkenyl, alkynyl, linear or branched aryl, $R_3$ can be H, alkyl, alkenyl, alkynyl, linear or branched aryl, $R_4$ can be H, $C_2$-$C_6$ alkyl, alkenyl, alkynyl, linear or branched aryl, $R_5$ can be H or alkyl, $R_6$ can be bicyclo[2.2.1]hept-5-enyl, and $R_7$ can be H, alkyl, alkenyl, alkynyl, linear or branched aryl.

In certain other embodiments, the present disclosure provides for fragrance or flavor compounds represented by Formula Ia, wherein $R_1$ can be H, alkyl, or C(O)$R_7$, $R_2$ can be alkyl, alkenyl, alkynyl, linear or branched aryl, $R_3$ can be H, alkyl, alkenyl, alkynyl, linear or branched aryl, $R_4$ can be alkyl, alkenyl, alkynyl, linear or branched aryl, $R_5$ can be H or alkyl, $R_6$ is cyclohexenyl, and $R_7$ can be H, alkyl, alkenyl, alkynyl, linear or branched aryl.

In certain other embodiments, the present disclosure provides for fragrance or flavor compounds represented by Formula Ia, wherein $R_1$ can be H, alkyl, or C(O)$R_7$, $R_2$ can be H, $C_2$-$C_6$ alkyl, alkenyl, alkynyl, linear or branched aryl, $R_3$ can be H, alkyl, alkenyl, alkynyl, linear or branched aryl, $R_4$ can be H, $C_2$-$C_6$ alkyl, alkenyl, alkynyl, linear or branched aryl, $R_5$ can be H or alkyl, $R_6$ can be cyclohexenyl, and $R_7$ can be H, alkyl, alkenyl, alkynyl, linear or branched aryl.

In certain other embodiments, the present disclosure provides for fragrance or flavor compounds represented by Formula Ia, wherein $R_1$ can be alkyl or C(O)$R_7$, $R_2$ can be H, alkyl, alkenyl, alkynyl, linear or branched aryl, $R_3$ can be H, alkyl, alkenyl, alkynyl, linear or branched aryl, $R_4$ can be H, alkyl, alkenyl, alkynyl, linear or branched aryl, $R_5$ can be H or alkyl, $R_6$ can be cyclohexenyl, and $R_7$ can be H, alkyl, alkenyl, alkynyl, linear or branched aryl.

In certain other embodiments, the present disclosure provides for fragrance or flavor compounds represented by Formula Ia, wherein $R_1$ can be H, alkyl or C(O)$R_7$, $R_2$ can be H, alkyl, alkenyl, alkynyl, linear or branched aryl, $R_3$ can be H, alkyl, alkenyl, alkynyl, linear or branched aryl, $R_4$ can be $C_3$-$C_6$ alkyl, alkenyl, alkynyl, linear or branched aryl, $R_5$ can be H or alkyl, $R_6$ can be cyclohexyl, and $R_7$ can be H, alkyl, alkenyl, alkynyl, linear or branched aryl.

In certain other embodiments, the present disclosure provides for a fragrance or flavor compound represented by Formula Ia, wherein $R_1$ can be alkyl, $R_2$ can be H, alkyl, alkenyl, alkynyl, linear or branched aryl, $R_3$ can be H, alkyl, alkenyl, alkynyl, linear or branched aryl, $R_4$ can be H, alkyl, alkenyl, alkynyl, linear or branched aryl, $R_5$ can be H or alkyl, and $R_6$ can be cyclohexyl.

In certain other embodiments, the present disclosure provides for a fragrance or flavor compound represented by Formula Ia, wherein $R_1$ can be C(O)$R_7$, $R_2$ can be H, $C_2$-$C_6$ alkyl, alkenyl, alkynyl, linear or branched aryl, $R_3$ can be H, alkyl, alkenyl, alkynyl, linear or branched aryl, $R_4$ can be H, alkyl, alkenyl, alkynyl, linear or branched aryl, $R_5$ can be H or alkyl, $R_6$ can be cyclohexyl, and $R_7$ can be H, alkyl, alkenyl, alkynyl, linear or branched aryl In certain other embodiments, the presently disclosed subject matter provides compounds of Formula Ib:

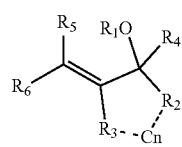

Formula Ib wherein n can be 1 or 2, $R_1$ can be H, alkyl, or $C(O)R_7$, $R_2$ can be alkyl, alkenyl, alkynyl, linear or branched aryl, $R_3$ can be alkyl, alkenyl, alkynyl, linear or branched aryl, $R_4$ can be H, alkyl, alkenyl, alkynyl, linear or branched aryl, $R_5$ can be H or alkyl, $R_6$ can be cyclohexyl, cyclohexenyl or bicyclo[2.2.1]hept-5-enyl, $R_7$ can be H, alkyl, alkenyl, alkynyl, linear or branched aryl, and wherein the compound of Formula Ib can be in a form of its racemates, its pure stereoisomers, enantiomers or diastereomers, or in a form of mixtures of stereoisomers, enantiomers or diastereomers, in any mixing ratio.

In certain embodiments the presently disclosed subject matter provides compounds of Formula IIa:

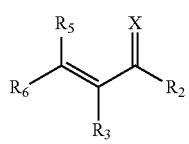

Formula IIa wherein X can be O, NOH, $NOCH_3$, or $NOCH_2$ (CO) $CH_3$, $R_2$ can be H, alkyl, alkenyl, alkynyl, linear or branched aryl, $R_3$ can be H, alkyl, alkenyl, alkynyl, linear or branched aryl, $R_5$ can be H, or alkyl, $R_6$ can be cyclohexyl, cyclohexenyl or bicyclo[2.2.1]hept-5-enyl, and wherein the compound of Formula IIa can be in a form of its racemates, its pure stereoisomers, enantiomers or diastereomers, or in a form of mixtures of stereoisomers, enantiomers or diastereomers, in any mixing ratio.

In certain other embodiments, the present disclosure provides for fragrance or flavor compounds represented by Formula IIa, wherein X can be NOH, $NOCH_3$, or $NOCH_2$ $(CO)CH_3$, n can be 1 or 2, $R_2$ can be H, $R_3$ can be H, alkyl, alkenyl, alkynyl, linear or branched aryl, $R_5$ can be H, alkyl, and $R_6$ can be cyclohexyl, cyclohexenyl or bicyclo[2.2.1]hept-5-enyl.

In certain other embodiments, the present disclosure provides for fragrance or flavor compounds represented by Formula IIa, wherein X can be $NOCH_3$, or $NOCH_2$ (CO) $CH_3$, n can be 1 or 2, $R_2$ can be alkyl, alkenyl, alkynyl, linear or branched aryl, $R_3$ can be H, alkyl, alkenyl, alkynyl, linear or branched aryl, $R_5$ can be H, alkyl, and $R_6$ can be cyclohexyl, cyclohexenyl or bicyclo[2.2.1]hept-5-enyl.

In certain other embodiments, the presently disclosed subject matter provides compounds of Formula IIb:

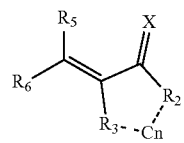

Formula IIb wherein X can be O, NOH, $NOCH_3$, or $NOCH_2$ (CO) $CH_3$, n can be 1 or 2, $R_2$ can be alkyl, alkenyl, alkynyl, linear or branched aryl, $R_3$ can be alkyl, alkenyl, alkynyl, linear or branched aryl, $R_5$ can be H, or alkyl, $R_6$ can be cyclohexyl, cyclohexenyl or bicyclo[2.2.1] hept-5-enyl, and wherein the compound of Formula IIb is in a form of its racemates, its pure stereoisomers, enantiomers or diastereomers, or in a form of mixtures of stereoisomers, enantiomers or diastereomers, in any mixing ratio.

In certain other embodiments, the present disclosure provides for fragrance or flavor compounds represented by Formula IIb, wherein X can be O, NOH, $NOCH_3$, or $NOCH_2$ $(CO)CH_3$, n can be 1 or 2, $R_2$ can be alkyl, alkenyl, alkynyl, linear or branched aryl, $R_3$ can be alkyl, alkenyl, alkynyl, linear or branched aryl, $R_5$ can be alkyl, and $R_6$ can be cyclohexyl, cyclohexenyl or bicyclo[2.2.1]hept-5-enyl.

In certain embodiments the presently disclosed subject matter provides compounds of Formula IIIa:

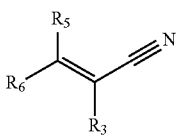

Formula IIIa wherein $R_3$ can be H, alkyl, alkenyl, alkynyl, linear or branched aryl, $R_5$ can be H, alkyl, $R_6$ can be cyclohexyl, cyclohexenyl or bicyclo[2.2.1]hept-5-enyl; and wherein the compound of Formula IIIa is in a form of its racemates, its pure stereoisomers, enantiomers or diastereomers, or in a form of mixtures of stereoisomers, enantiomers or diastereomers, in any mixing ratio.

The presently disclosed subject matter also provides for fragrance or flavor compositions comprising one or more compounds Formula Ia, Formula Ib, Formula IIa, Formula IIb, or Formula IIIa.

In particular embodiments, the present disclosure provides for fragrance compositions, wherein the concentration of the compounds of Formula Ia, Formula Ib, Formula IIa, Formula IIb, or Formula IIIa can be from about 0.01% to about 20% by weight of the fragrance composition.

In certain embodiments, the present disclosure provides for fragrance compositions comprising one or more compounds Formula Ia, Formula Ib, Formula IIa, Formula IIb, or Formula IIIa and further comprising one or more compounds selected from the group consisting of one or more aldehydic compound(s), one or more animalic compound(s), one or more balsamic compound(s), one or more citrus compound(s), one or more floral compound(s), one or more fruity compound(s), one or more gourmand compound(s), one or more green compound(s), one or more herbaceous compound(s), one or more marine compound(s), one or more mossy compound(s), one or more musk compound(s), one or more piney compound(s), one or more powdery compound(s), one or more spicy compound(s) and/or one or more woody and/or amber compound(s), and combinations thereof.

In certain other embodiments, the present disclosure provides for flavor compositions, wherein the concentration of the compound of Formula Ia, Formula Ib, Formula IIa, Formula IIb, or Formula IIIa can be from about 0.001% to about 20% by weight of the flavor composition. In a particular embodiment, the flavor composition can further comprise a flavor carried.

Another aspect of the present disclosure provides a consumer product that can include one or more compounds of Formula Ia, Formula Ib, Formula IIa, Formula IIb, or Formula IIIa. In certain other embodiments, the present disclosure provides a consumer product that can include a fragrance or flavor composition comprising one or more compounds of Formula Ia, Formula Ib, Formula IIa, Formula IIb, or Formula IIIa.

DETAILED DESCRIPTION

As noted above, there remains a need and demand in the art for unique fragrance and flavor compositions. The presently disclosed subject matter addresses these needs through compounds disclosed herein and/or new fragrance and flavor compositions comprising one or more of the disclosed compounds.

For clarity, and not by way of limitation, the detailed description is divided into the following subsections:
1. Definitions;
2. Fragrance and Flavor Compounds;
3. Fragrance Compositions;
4. Use of Fragrance Compositions in Consumer Products; and
5. Flavor Compositions.

1. Definitions

The terms used in this specification generally have their ordinary meanings in the art, within the context of this disclosure and in the specific context where each term is used. Certain terms are discussed below, or elsewhere in the specification, to provide additional guidance to a person of ordinary skill in the art describing the compounds, compositions and methods of the disclosure and how to make and use them.

As used herein, the use of the word "a" or "an" when used in conjunction with the term "comprising" in the claims and/or the specification can mean "one," but it is also consistent with the meaning of "one or more," "at least one," a plurality, and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "enantiomers" refers to a pair of stereoisomers that are non-superimposable mirror images of each other. A 1:1 mixture of a pair of enantiomers is a "racemic" mixture or a racemate. The term is used to designate a racemic mixture where appropriate.

As used herein, the term "enantiopure" refers to a sample that within the limits of detection consists of a single enantiomer.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro or levorotatory) in which they rotate plane polarized light at the wavelength of the sodium D line. The compounds of the presently disclosed subject matter contain one or more asymmetric centers and can thus give rise to enantiomers, diastereomers, and other stereoisomeric forms that can be defined, in terms of absolute stereochemistry, as (R)- or(S)-. The presently disclosed subject matter is meant to include all such possible isomers, including racemic mixtures, optically pure forms, and intermediate mixtures. Optically active (R)- and(S)-isomers can be prepared using chiral synthons or chiral reagents or resolved using conventional techniques. If the compound contains a double bond, the substituent can be E or Z configuration. If the compound contains a disubstituted cycloalkyl, the cycloalkyl substituent can have a cis- or trans-configuration. All tautomeric forms are also intended to be included.

As used herein, the term "isomers" refers to different compounds that have the same molecular formula but differ in arrangement and configuration of the atoms. Also, as used herein, the term "stereoisomer" refers to any of the various stereo isomeric configurations which can exist for a given compound of the presently disclosed subject matter and includes geometric isomers. It is understood that a substituent can be attached at a chiral center of a carbon atom. Therefore, the presently disclosed subject matter includes enantiomers, diastereomers, or racemates of the compound. Also, as used herein, the terms "constitutional isomers" refers to different compounds which have the same numbers of, and types of, atoms but the atoms are connected differently.

As used herein, the term "fragrance composition" refers to a mixture comprising one or more fragrance compounds, in any of their forms, and one or more solvents or perfuming co-ingredients. As known in the art, a fragrance composition contains one or more fragrance compounds in order to impart an olfactory note to the consumer product formulation (e.g., a household cleaner, perfume, or other consumer product) to which it is added. In one embodiment, the fragrance composition contains two or more fragrance compounds which, collectively and in combination with the solvent to which they are added, impart an intended olfactory note (e.g., a hedonically pleasing "tropical" note) to a human in close proximity to the fragrance composition. In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin, and are known to perfumers of ordinary skill in the art. Many of these ingredients are listed in reference texts such as S. Arctander, *Perfume and Flavor Chemicals,* 1969, Montclair, New Jersey, USA or any of its more recent versions, each of which are hereby incorporated by reference in their entireties.

As used herein, the term "accord" refers to a mixture of two or more different fragrance compounds that creates a specific smell, odor or scent. One or more "accords" can be utilized as part of fragrance composition.

As used herein, the term "flavor composition" refers to a composition that contains one or more compounds (e.g., co-ingredients) that provide a desired taste when combined with a solvent that is suitable for oral administration and oral consumption. Examples of flavoring co-ingredients that are generally included in a flavor composition are listed in S. Arctander, *Perfume and Flavor Chemicals,* 1969, Montclair, New Jersey, USA or any of its more recent versions, each of which are hereby incorporated by reference in their entireties. The skilled person in the art of flavors is able to select them on the basis of its general knowledge and according to the nature of the product to be flavored and the desired taste.

As used herein, the term "organoleptic effective quantity" refers to the amount of a compound in a flavor composition in which the individual component will contribute its characteristic flavor properties.

As used herein, the term "organoleptic effect" or "taste profile" of the flavor composition refers to the sum of the effects of all flavor ingredients present.

As used herein, the term "consumer product" or "end product" refers to a composition that is in a form ready for use by the consumer for the marketed indication. A solvent suitable for use in a consumer product is a solvent that, when combined with other components of the end product, will not render the consumer product unfit for its intended consumer use.

2. Fragrance and Flavor Compounds

The present disclosure is directed to the synthesis and application of fragrance and/or flavor compounds having unique and desired fragrance and/or flavor characteristics.

In certain embodiments, the presently disclosed subject matter provides compounds represented by Formula I:

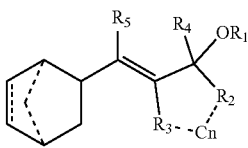

Formula I

More particularly, in certain embodiments the presently disclosed subject matter provides compounds of Formula Ia:

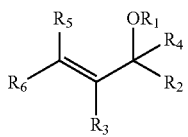

Formula Ia wherein $R_1$ can be H, alkyl or $C(O)R_7$;
wherein $R_2$ can be H, alkyl, alkenyl, alkynyl, linear or branched aryl;
wherein $R_3$ can be H, alkyl, alkenyl, alkynyl, linear or branched aryl;
wherein $R_4$ can be H, alkyl, alkenyl, alkynyl, linear or branched aryl;
wherein $R_5$ can be H or alkyl;
wherein $R_6$ can be cyclohexyl, cyclohexenyl or bicyclo[2.2.1]hept-5-enyl; and
wherein $R_7$ can be H, alkyl, alkenyl, alkynyl, linear or branched aryl.

In a specific embodiment, the present disclosure provides a compound of Formula Ia, wherein $R_1=R_2=R_3=R_5=H$, $R_4$-methyl, and $R_6$=cyclohexenyl. In another specific embodiment, the present disclosure provides a compound of Formula Ia, wherein $R_1=C(O)R_7$, $R_2=R_7$-methyl, $R_3=R_4=R_5=H$, and $R_6$=cyclohexenyl. In another specific embodiment, the present disclosure provides a compound of Formula Ia, wherein $R_1=R_2$-methyl, $R_3=R_4=R_5=H$, and $R_6$=cyclohexenyl. In another specific embodiment, the present disclosure provides a compound of Formula Ia, wherein $R_1=R_3=R_5=H$, $R_2=R_4$=methyl, and $R_6$=cyclohexenyl. In another specific embodiment, the present disclosure provides a compound of Formula Ia, wherein $R_1=R_3=R_5=H$, $R_2$=methyl, $R_4$-ethyl, and $R_6$-cyclohexenyl. In another specific embodiment, the present disclosure provides a compound of Formula Ia, wherein $R_1=R_3=R_5=H$, $R_2$-methyl, $R_4$=vinyl, and $R_6$=cyclohexenyl. In another specific embodiment, the present disclosure provides a compound of Formula Ia, wherein $R_1=R_3=R_5=H$, $R_2$=methyl, $R_4$=isopropyl, and $R_6$=cyclohexenyl. In another specific embodiment, the present disclosure provides a compound of Formula Ia, wherein $R_1=R_3=R_5=H$, $R_2$=methyl, $R_4$=propyl, and $R_6$=cyclohexenyl. In another specific embodiment, the present disclosure provides a compound of Formula Ia, wherein $R_1=R_2=R_4=R_5=H$, $R_3$=methyl, and $R_6$=cyclohexenyl. In another specific embodiment, the present disclosure provides a compound of Formula Ia, wherein $R_1=C(O)R_7$, $R_2=R_4=R_5=H$, $R_3$-methyl, $R_6$=cyclohexenyl, and $R_7$-methyl. In another specific embodiment, the present disclosure provides a compound of Formula Ia, wherein $R_1=R_3$=methyl, $R_2=R_4=R_5=H$, and $R_6$=cyclohexenyl. In another specific embodiment, the present disclosure provides a compound of Formula Ia, wherein $R_1=R_2=R_5=H$, $R_3=R_4$=methyl, and $R_6$-cyclohexenyl. In another specific embodiment, the present disclosure provides a compound of Formula Ia, wherein $R_1=R_2=R_5=H$, $R_3$-methyl, $R_4$-ethyl, and $R_6$=cyclohexenyl. In another specific embodiment, the present disclosure provides a compound of Formula Ia, wherein $R_1=R_2=R_5=H$, $R_3$-methyl, $R_4$=propyl, and $R_6$=cyclohexenyl. In another specific embodiment, the present disclosure provides a compound of Formula Ia, wherein $R_1=R_2=R_5=H$, $R_3$-methyl, $R_4$=allyl, and $R_6$=cyclohexenyl. In another specific embodiment, the present disclosure provides a compound of Formula Ia, wherein $R_1=R_3=R_4=R_5=H$, $R_2$=methyl, and $R_6$-bicyclo[2.2.1]hept-5-enyl. In another specific embodiment, the present disclosure provides a compound of Formula Ia, wherein $R_1=C(O)R_7$, $R_2=R_7$-methyl, $R_3=R_4=R_5=H$, and $R_6$=bicyclo[2.2.1]hept-5-enyl. In another specific embodiment, the present disclosure provides a compound of Formula Ia, wherein $R_1=R_2$=methyl, $R_3=R_4=R_5=H$, and $R_6$=bicyclo[2.2.1]hept-5-enyl. In another specific embodiment, the present disclosure provides a compound of Formula Ia, wherein $R_1=R_3=R_5=H$, $R_2=R_4$=methyl, and $R_6$-bicyclo[2.2.1]hept-5-enyl. In another specific embodiment, the present disclosure provides a compound of Formula Ia, wherein $R_1=R_3=R_5=H$, $R_2$-methyl, $R_4$-ethyl, and $R_6$-bicyclo[2.2.1]hept-5-enyl. In another specific embodiment, the present disclosure provides a compound of Formula Ia, wherein $R_1=R_3=R_5=H$, $R_2$=methyl, $R_4$=vinyl, and $R_6$=bicyclo[2.2.1]hept-5-enyl. In another specific embodiment, the present disclosure provides a compound of Formula Ia, wherein $R_1=R_3=R_5=H$, $R_2$=methyl, $R_4$=isopropyl, and $R_6$=bicyclo[2.2.1]hept-5-enyl. In another specific embodiment, the present disclosure provides a compound of Formula Ia, wherein $R_1=R_3=R_5=H$, $R_2$=methyl, $R_4$=propyl, and $R_6$=bicyclo[2.2.1]hept-5-enyl. In another specific embodiment, the present disclosure provides a compound of Formula Ia, wherein $R_1=R_2=R_4=R_5=H$, $R_3$-methyl, and $R_6$-bicyclo[2.2.1]hept-5-enyl. In another specific embodiment, the present disclosure provides a compound of Formula Ia, wherein $R_1=C(O)R_7$, $R_2=R_4=R_5=H$, $R_3$=methyl, $R_6$=bicyclo[2.2.1]hept-5-enyl, and $R_7$=methyl. In another specific embodiment, the present disclosure provides a compound of Formula Ia, wherein $R_1=R_3=R_4=R_5=H$, $R_2$-methyl, and $R_6$=cyclohexyl. In another specific embodiment, the present disclosure provides a compound of Formula Ia, wherein $R_1$=C(O)$R_7$, $R_2$=$R_7$=methyl, $R_3$=$R_4$=$R_5$=H, and $R_6$=cyclohexyl. In another specific embodiment, the present disclosure provides a compound of Formula Ia, wherein $R_1$=$R_2$=methyl, $R_3$=$R_4$=$R_5$=H, and $R_6$-cyclohexyl. In another specific embodiment, the present disclosure provides a compound of Formula Ia, wherein $R_1$=$R_3$=$R_5$=H, $R_2$-methyl, $R_4$-methyl, and $R_6$-cyclohexyl. In another specific embodiment, the present disclosure provides a compound of Formula Ia, wherein $R_1$=$R_3$=$R_5$=H, $R_2$-methyl, $R_4$-ethyl, and $R_6$=cyclohexyl. In another specific embodiment, the present disclosure provides a compound of Formula Ia, wherein $R_1$=$R_3$=$R_5$=H, $R_2$=methyl, $R_4$-isopropyl, and $R_6$-cyclohexyl. In another specific embodiment, the present disclosure provides a compound of Formula Ia, wherein $R_1$-$R_3$=$R_5$=H, $R_2$-methyl, $R_4$-propyl, and $R_6$=cyclohexyl. In another specific embodiment, the present disclosure provides a compound of Formula Ia, wherein $R_1$=$R_2$=$R_4$=$R_5$=H, $R_3$-methyl, and $R_6$=cyclohexyl. In another specific embodiment, the present disclosure provides a compound of Formula Ia, wherein $R_1$=C(O)$R_7$, $R_2$=$R_4$=$R_5$=H, $R_3$=$R_7$-methyl, and $R_6$=cyclohexyl.

In certain other embodiments, the presently disclosed subject matter provides compounds of Formula Ib:

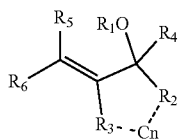

Formula Ib wherein n can be 1 or 2;
wherein $R_1$ can be H, alkyl or C(O)$R_7$;
wherein $R_2$ can be alkyl, alkenyl, alkynyl, linear or branched aryl;
wherein $R_3$ can be alkyl, alkenyl, alkynyl, linear or branched aryl;
wherein $R_4$ can be H, alkyl, alkenyl, alkynyl, linear or branched aryl;
wherein $R_5$ can be H or alkyl;
wherein $R_6$ can be cyclohexyl, cyclohexenyl or bicyclo[2.2.1]hept-5-enyl; and
wherein $R_7$ can be H, alkyl, alkenyl, alkynyl, linear or branched aryl.

In a specific embodiment, the present disclosure provides a compound of Formula Ib, wherein n=1, $R_1$=$R_4$=$R_5$=H, $R_2$=$R_3$-methyl, and $R_6$-cyclohexenyl. In another specific embodiment, the present disclosure provides a compound of Formula Ib, wherein n=1, $R_1$=C(O)$R_7$, $R_2$-$R_3$=$R_7$-methyl, $R_4$=$R_5$=H, and $R_6$-cyclohexenyl. In another specific embodiment, the present disclosure provides a compound of Formula Ib, wherein n=1, $R_1$=$R_2$=$R_3$=methyl, $R_4$-$R_5$=H, and $R_6$-cyclohexenyl. In another specific embodiment, the present disclosure provides a compound of Formula Ib, wherein n=2, $R_1$=$R_4$=$R_5$=H, $R_2$=$R_3$-methyl, and $R_6$-cyclohexenyl. In another specific embodiment, the present disclosure provides a compound of Formula Ib, wherein n=2, $R_1$—C(O)$R_7$, $R_2$=$R_3$=$R_7$-methyl, $R_4$=$R_5$=H, and $R_6$-cyclohexenyl. In another specific embodiment, the present disclosure provides a compound of Formula Ib, wherein n=2, $R_1$=$R_2$=$R_3$=methyl, $R_4$=$R_5$=H, and $R_6$-cyclohexenyl.

In certain embodiments, the presently disclosed subject matter provides compounds represented by Formula II:

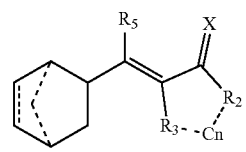

Formula II

More particularly, in certain embodiments the presently disclosed subject matter provides compounds of Formula IIa:

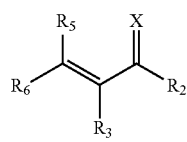

Formula IIa wherein X can be O, NOH, NOCH$_3$ or NOCH$_2$ (CO)CH$_3$;
wherein $R_2$ can be H, alkyl, alkenyl, alkynyl, linear or branched aryl;
wherein $R_3$ can be H, alkyl, alkenyl, alkynyl, linear or branched aryl;
wherein $R_5$ can be H or alkyl; and
wherein $R_6$ can be cyclohexyl, cyclohexenyl or bicyclo[2.2.1]hept-5-enyl.

In a specific embodiment, the presently disclosed subject matter provides the compound of Formula IIa, wherein X=NOH, $R_2$=methyl, $R_3$=$R_5$=H, and $R_6$=cyclohexenyl. In another specific embodiment, the presently disclosed subject matter provides the compound of Formula IIa, wherein X=NOCH$_3$, $R_2$=methyl, $R_3$=$R_5$=H, and $R_6$=cyclohexenyl. In another specific embodiment, the presently disclosed subject matter provides the compound of Formula IIa, wherein X=O, $R_2$=$R_5$=H, $R_3$=methyl, and $R_6$=cyclohexenyl. In another specific embodiment, the presently disclosed subject matter provides the compound of Formula IIa, wherein X=NOH, $R_2$=$R_5$=H, $R_3$-methyl, and $R_6$=cyclohexenyl. In another specific embodiment, the presently disclosed subject matter provides the compound of Formula IIa, wherein X=NOCH$_3$, $R_2$=$R_5$=H, $R_3$=methyl, and $R_6$=cyclohexenyl. In another specific embodiment, the presently disclosed subject matter provides the compound of Formula IIa, wherein X=O, $R_2$=methyl, $R_3$=$R_5$=H, and $R_6$=bicyclo[2.2.1]hept-5-enyl. In another specific embodiment, the presently disclosed subject matter provides the compound of Formula IIa, wherein X=NOCH$_3$, $R_2$-methyl, $R_3$=$R_5$=H, and $R_6$=bicyclo[2.2.1]hept-5-enyl. In another specific embodiment, the presently disclosed subject matter provides the compound of Formula IIa, wherein X=O, $R_2$=$R_5$=H, $R_3$=methyl, and $R_6$=bicyclo[2.2.1]hept-5-enyl. In another specific embodiment, the presently disclosed subject matter provides the compound of Formula IIa, wherein X=O, $R_2$-methyl, $R_3$=$R_5$=H, and $R_6$=cyclohexyl. In another specific embodiment, the presently disclosed subject matter provides the compound of Formula IIa, wherein X=NOH, $R_2$-methyl, $R_3$=$R_5$=H, and $R_6$=cyclohexyl. In another specific embodiment, the presently disclosed subject matter provides the compound of Formula IIa, wherein X=NOCH$_3$, $R_2$-methyl, $R_3$=$R_5$=H, and $R_6$=cyclohexyl. In another specific embodiment, the presently disclosed subject matter provides the compound of Formula IIa, wherein X=O, $R_2$=$R_5$=H, $R_3$=methyl, and $R_6$=cyclohexyl. In another specific embodiment, the presently disclosed subject matter provides the compound of Formula IIa, wherein X=NOH, $R_2$=$R_5$=H, $R_3$=methyl, and $R_6$=bicyclo[2.2.1]hept-5-enyl. In another specific embodiment, the presently disclosed subject matter provides the compound of Formula IIa, wherein X=NOH, $R_2$=$R_5$=H, $R_3$-methyl, and $R_6$=cyclohexyl.

In certain other embodiments, the presently disclosed subject matter provides compounds of Formula IIb:

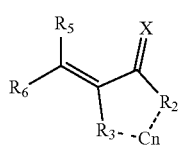

Formula IIb wherein X can be O, NOH, $NOCH_3$ or $NOCH_2$ $(CO)CH_3$;
wherein n can be 1 or 2;
wherein $R_2$ can be alkyl, alkenyl, alkynyl, linear or branched aryl;
wherein $R_3$ can be alkyl, alkenyl, alkynyl, linear or branched aryl;
wherein $R_5$ can be H or alkyl; and
wherein $R_6$ can be cyclohexyl, cyclohexenyl or bicyclo[2.2.1]hept-5-enyl.

In a specific embodiment, the presently disclosed subject matter provides the compound of Formula IIb, wherein n=1, X=O, $R_2$=$R_3$=methyl, $R_5$=H, and $R_6$-cyclohexenyl. In another specific embodiment, the presently disclosed subject matter provides the compound of Formula IIb, wherein n=2, X=O, $R_2$=$R_3$-methyl, $R_5$=H, and $R_6$=cyclohexenyl.

In certain embodiments, the presently disclosed subject matter provides compounds represented by Formula III:

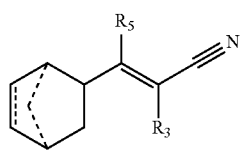

Formula III

More particularly, in certain embodiments the presently disclosed subject matter provides compounds of Formula IIIa:

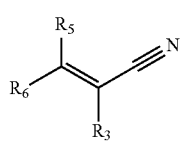

Formula IIIa wherein $R_3$ can be H, alkyl, alkenyl, alkynyl, linear or branched aryl;
wherein $R_5$ can be H or alkyl; and
wherein $R_6$ can be cyclohexyl, cyclohexenyl or bicyclo[2.2.1]hept-5-enyl.

In a specific embodiment, the presently disclosed subject matter provides a compound of Formula IIIa, wherein $R_3$-methyl, $R_5$=H, and $R_6$=cyclohexenyl. In another specific embodiment, the presently disclosed subject matter provides the compound of Formula IIIa, wherein $R_3$-methyl, $R_5$=H, and $R_6$=bicyclo[2.2.1]hept-5-enyl. In another specific embodiment, the presently disclosed subject matter provides the compound of Formula IIIa, wherein $R_3$=methyl, $R_5$=H, and $R_6$=cyclohexyl.

In certain embodiments, the compound includes constitutional isomers, enantiomers, stereoisomers, and racemic mixtures of said compound.

The presently disclosed compounds can be synthetic or natural. Synthetic versions of the compounds include those obtained via chemical synthesis or isolated through chemical processes, whether artificial or nature-identical. Natural versions of the presently disclosed compounds include those obtained via physical, enzymatic and/or microbiological processes, e.g., fermentation, from materials of a plant or animal origin.

3. Fragrance Compositions

In certain embodiments, any one of the above described compounds can be provided in a fragrance composition. Certain embodiments of the presently disclosed subject matter provide a method to modify, enhance or improve the odor properties of a fragrance composition by adding to the composition an effective quantity of one or more of the compounds.

For fragrance applications, concentrations of the compounds of Formulas I-III are based on the total weight of the composition into which the fragrance compound is incorporated. Typical concentrations of the compounds of the present disclosure in a fragrance composition can range from about 0.01% to about 20%, or from about 0.01% to about 10%, or from about 0.01% to about 5%, or from about 0.01% to about 3%, or from about 0.01% to about 1%, based on the total weight of the fragrance composition into which the fragrance compound is incorporated. In particular embodiments, the presently disclosed compounds can be present in the fragrance composition in an amount of about 0.01%, about 0.1%, about 0.5%, about 0.8%, about 1%, about 3%, or about 5% by weight, based on the total weight of the fragrance composition. In further embodiments, the presently disclosed compounds can be present in the fragrance composition in an amount of at least about 0.01%, at least about 0.1%, at least about 0.5%, at least about 1%, or at least about 5% by weight, based on the total weight of the fragrance composition. Those skilled in the art are able to employ the desired level of the compound of the presently disclosed subject matter to provide the desired fragrance/flavor and intensity.

The compounds of the presently disclosed subject matter can be combined with one or more fragrance compounds from various fragrance categories to form accords or fragrance compositions, such fragrance categories including but not limited to one or more aldehydic compound(s), one or more animalic compound(s), one or more balsamic compound(s), one or more citrus compound(s), one or more floral compound(s), one or more fruity compound(s), one or more gourmand compound(s), one or more green compound(s), one or more herbaceous compound(s), one or more marine compound(s), one or more mossy compound(s), one or more musk compound(s), one or more piney compound(s), one or more powdery compound(s), one or more spicy compound(s), and/or one or more woody and/or amber compound(s), and combinations thereof.

In certain embodiments, the fragrance composition can include a compound of Formulas I-III and one or more fragrance compounds including one or more citrus compound(s), one or more floral compound(s), one or more fruity compound(s), one or more gourmand compound(s), one or more green compound(s), one or more herbal compound(s), one or more musk compound(s), and one or more woody and/or amber compound(s). The compound(s) of Formulas I-III can be present in an amount of from about 0.0001% to about 5%, from about 0.001% to about 5%, or from about 0.01% to about 1% by weight, based on the total weight of the fragrance composition. The one or more citrus compound(s) can be present in an amount of from about 1% to about 20%, from about 1% to about 15%, or from about 1% to about 10% by weight, based on the total weight of the fragrance composition. The one or more floral compound(s) can be present in an amount of from about 1% to about 50%, from about 5% to about 45%, or from about 15% to about 40% by weight, based on the total weight of the fragrance composition. The one or more fruity compound(s) can be present in an amount of from about 1% to about 30%, from about 5% to about 25%, from about 10% to about 20%, or from about 15% to about 20% by weight, based on the total weight of the fragrance composition. The one or more gourmand compound(s) can be present in an amount of from about 0.01% to about 5%, from about 0.2% to about 2%, or from about 0.5% to about 1.5% by weight, based on the total weight of the fragrance composition. The one or more green compound(s) can be present in an amount of from about 0.01% to about 5%, from about 0.2% to about 3%, or from about 0.5% to about 2.5% by weight, based on the total weight of the fragrance composition. The one or more herbal compound(s) can be present in an amount of from about 0.01% to about 5%, from about 0.1% to about 2%, from about 0.2% to about 1.5%, or from about 0.3% to about 0.5% by weight, based on the total weight of the fragrance composition. The one or more musk compound(s) can be present in an amount of from about 1% to about 10%, from about 2% to about 8%, or from about 4% to about 6% by weight, based on the total weight of the fragrance composition. The one or more woody and/or compound(s) can be present in an amount of from about 5% to about 25%, from about 10% to about 20%, or from about 12% to about 18% by weight, based on the total weight of the fragrance composition. In a specific embodiment, the compound of Formulas I-III can be 4-(cyclohex-3-en-1-yl) but-3-en-2-yl acetate. In certain embodiments, the one or more solvents can include dipropylene glycol (DPG).

In certain embodiments, the fragrance composition can include a compound of Formulas I-III and one or more fragrance compounds including one or more aldehydic compound(s), one or more citrus compound(s), one or more floral compound(s), one or more fruity compound(s), one or more green compound(s), one or more herbal compound(s), one or more musk compound(s), and one or more piney compound(s). The compound(s) of Formulas I-III can be present in an amount of from about 1% to about 25%, from about 5% to about 15%, or about 10% by weight, based on the total weight of the fragrance composition. The one or more aldehydic compound(s) can be present in an amount of from about 1% to about 10%, from about 2% to about 5%, or from about 3% to about 4% by weight, based on the total weight of the fragrance composition. The one or more citrus compound(s) can be present in an amount of from about 10% to about 50%, from about 20% to about 45%, or from about 30% to about 40% by weight, based on the total weight of the fragrance composition. The one or more floral compound(s) can be present in an amount from about 5% to about 35%, from about 15% to about 30%, or about 25% by weight, based on the total weight of the fragrance composition. The one or more fruity compound(s) can be present in an amount of from about 0.1% to about 2%, from about 0.2% to about 1.5%, or from about 0.3% to about 0.5% by weight, based on the total weight of the fragrance composition. The one or more green compound(s) can present in an amount of from about 0.1% to about 2%, from about 0.3% to about 1.5%, or from about 0.5% to about 1% by weight, based on the total weight of the fragrance composition. The one or more herbal compound(s) can be present in an amount of from about 1% to about 10%, from about 2% to about 8%, or from about 3% to about 5% by weight, based on the total weight of the fragrance composition. The one or more musk compound(s) can be present in an amount of from about 1% to about 20%, from about 3% to about 15%, or from about 5% to about 10% by weight, based on the total weight of the fragrance composition. The one or more piney compound(s) can be present in an amount of from about 5% to about 25%, from about 10% to about 20%, or from about 12% to about 15% by weight, based on the total weight of the fragrance composition. In a specific embodiment, the compound of Formulas I-III can be 4-(cyclohex-3-en-1-yl) but-3-en-2-yl acetate. In certain embodiments, the one or more solvents can include dipropylene glycol (DPG).

In certain embodiments, the fragrance composition can include a compound of Formulas I-III and one or more fragrance compounds including one or more citrus compound(s), one or more floral compound(s), one or more fruity compound(s), one or more gourmand compound(s), one or more green compound(s), one or more musk compound(s), and one or more woody and/or amber compound(s). The compound(s) of Formulas I-III can be present in an amount of from about 1% to about 25%, from about 5% to about 15%, or about 10% by weight, based on the total weight of the fragrance composition. The one or more citrus compound(s) can be present in an amount of from about 1% to about 25%, from about 5% to about 20%, or from about 10% to about 15% by weight, based on the total weight of the fragrance composition. The one or more floral compound(s) can be present in an amount of from about 15% to about 40%, from about 20% to about 35%, or from about 25% to about 30% by weight, based on the total weight of the fragrance composition. The one or more fruity compound(s) can be present in an amount from about 25% to about 50%, or from about 30% to about 45%, or from about 35% to about 40% by weight, based on the total weight of the fragrance composition. The one or more gourmand compound(s) can be present in an amount of from about 0.01% to about 1.5%, or from about 0.1% to about 1%, or about 0.5% by weight, based on the total weight of the fragrance composition. The one or more green compound(s) can be present in an amount of from about 0.01% to about 5%, from about 0.2% to about 3%, or from about 0.5% to about 2.5% by weight, based on the total weight of the fragrance composition. The one or more musk compound(s) can be present in an amount of from about 0.1% to about 10%, from about 1% to about 5%, or from about 2% to about 4% by weight, based on the total weight of the fragrance composition. The one or more woody and/or amber compound(s) can be present in an amount of from about 0.01% to about 5%, from about 0.05% to about 2%, or from about 0.1% to about 1% by weight, based on the total weight of the fragrance composition. In a specific embodiment, the compound of Formulas I-III can be 4-(cyclohex-3-en-1-yl) but- 3-en-2-yl acetate. In certain embodiments, the one or more solvents can include dipropylene glycol (DPG).

In certain embodiments, the fragrance composition can include a compound of Formulas I-III and one or more fragrance compounds including one or more citrus compound(s), one or more floral compound(s), one or more fruity compound(s), one or more gourmand compound(s), one or more musk compound(s), and one or more woody and/or amber compound(s). The compound(s) of Formulas I-III can be present in an amount of from 0.1% to about 10%, from about 1% to about 5%, or about 2% by weight, based on the total weight of the fragrance composition. The one or more citrus compound(s) can be present in an amount of from about 1% to about 25%, from about 5% to about 20%, or from about 10% to about 15% by weight, based on the total weight of the fragrance composition. The one or more floral compound(s) can be present in an amount of from about 10% to about 50%, from about 20%, to about 40%, or from about 30% to about 35% by weight, based on the total weight of the fragrance composition. The one or more fruity compound(s) can be present in an amount of from about 0.01% to about 5%, from about 0.1% to about 2%, from about 0.2% to about 1.5%, or from about 0.3% to about 0.5% by weight, based on the total weight of the fragrance composition. The one or more gourmand compound(s) can be present in an amount of from about 0.01% to about 5%, from about 0.1% to about 2%, from about 0.2% to about 1.5%, or from about 0.3% to about 0.5% by weight, based on the total weight of the fragrance composition. The one or more musk compound(s) can be present in an amount of from about 0.0001% to about 5%, from about 0.001 to about 3%, or from about 0.01% to about 1% by weight, based on the total weight of the fragrance composition. The one or more woody and/or amber compound(s) can be present in an amount of from about 0.01% to about 15%, from about 0.1% to about 10%, or from about 1% to about 5% by weight, based on the total weight of the fragrance composition. In a specific embodiment, the compound of Formulas I-III can be 1-(cyclohex-3-en-1-yl)-2-methylpent-1-en-3-ol. In certain embodiments, the one or more solvents can include dipropylene glycol methyl ether acetate (DPMA).

Non-limiting examples of suitable aldehydic compounds include acetaldehyde C-8, acetacldeyde C-9, acetaldehyde C-10, adoxal, aldehyde C-8, aldehyde C-9, aldehyde C-10, aldehyde C-11, aldehyde C-12, aldehyde C-12 lauric, aldehyde C-12 MNA, aldehyde supra, cyclomyral trans-2-decenal, trans-4-decenal cis-4-decenal, 9-decenal, myrac aldehyde, precyclemone B, trans-2-decenal, undecylenic aldehyde, 1-methyl-4-(4-methylpentyl)cyclohex-3-ene-1-carbaldehyde (VERNALDEHYDE®), and combinations thereof.

Non-limiting examples of suitable animalic compound include 5-cyclohexadecen-1-one (AMBRETONE®), 17-oxacycloheptadec-6-en-1-one (ambrettolide), 2,5,5-trimethyl-1,3,4,4a,6,7-hexahydronaphthalen-2-ol (ambrinol), 2-Methyl-5-(5,5,6-trimethylbicyclo[2.2.1]hept-2-yl)cyclohexanone (ALDRON®), civet, p-cresol, cresyl methyl ether, indole, skatole, and combinations thereof.

Non-limiting examples of suitable balsamic compounds include benzy salicylate, cylohexyl salicylate, isopropoxy ethyl salicylate, phenethyl salicylate, styrax oil, and combinations thereof.

Non-limiting examples of suitable citrus compounds include delta-3-carene, citral, citronellal, L-citronellol, decanal, DH-L-citronellal, DH-myrcenol, limonene, myrcenol, nootkatone, sinensal, bergamot oil, grapefruit oil, lemon oil, lime oil, orange oil, tridecene-2-nitrile, and/or yuzu core base.

Non-limiting examples of suitable floral compounds include acetanisole, alpha amyl cinnamaldehyde, anisyl acetate, anisic aldehyde, benzyl acetate, bourgeonal, butyl acetate, hexyl cinammic aldehyde, 1-citrol, cyclamen aldehyde, cyclohexyl lactone, delta-damascone, 9-decen-1-ol, dimethyl benzyl carbinol, dimethyl octanol (tetrahydro geraniol), farnesal, 1-dihydrofarnesal, ethyl linalool, 1-farnesal, farnesol, 1-dihydrofarnesol, 3-(3-Isopropylphenyl) butanal (FLORHYDRAL®), 3-(4-ethylphenyl)-2,2-dimethylpropanal (floralozone), 4-methyl-2-(2-methylpropyl) oxan-4-ol (FLOROL®), geraniol, gernayl acetate, piperonal, methyl 3-oxo-2-pentylcyclopentaneacetate (Hedione®), 2-Methyl-3-(3,4-methylenedioxyphenyl) propanal (Heliobouquet), 1-(5,6,7,8-tetrahydronaphthalen-2-yl) ethanone (FLORANTONE®), 3-(4-Isobutyl-phenyl)-2-methyl-propionaldehyde (SUZARAL®), isobutyl salicylate, hexyl cinnamaldehyde, hexyl salicylate, indole, alpha-ionone, beta-ionone, isopropoxy ethyl salicylate, methyl-2-((1S*, 2R*)-3-oxo-2-pentylcyclopentyl)acetate (JASMODIONE®), cis-jasmone, 4-(4-hydroxy-4-methylpentyl)cyclohex-3-ene-1-carbaldehyde (KOVANOL®), laurinal, lilial, linalool, linalyl acetate, 2,4,6,-trimethyl-4-phenyl-1,3-dioxane (LOREXAN®), 2,4-Dimethyl-4,4a,5,9b-tetrahydroindeno[1,2-d][1,3]dioxine (Magnolan), (4-propan-2-ylcyclohexyl) methanol (Mayol), methyl dihydrojasomante, gamma-methyl ionone, methyl benzoate, 1-(4-Isopropylcyclohexyl) ethanol (Mugetanol), nerol, 1-(3-Methyl-benzofuran-2-yl)-ethanone (Nerolione), neryl acetate, orantha, L., 2-pentyl cyclopentanone, 2-cyclohexyl-2-cyclohexylideneacetonitrile (PEONILE®), phenoxanol, phenoxy ethyl isobutyrate, phenylacetaldehyde, phenyl ethyl alcohol, prenyl salicylate, rose oxide, rosephenone, rosyrane, terpineol, undecavertol, 2,2,5-trimethyl-5-pentylcyclopentan-1-one (VELOUTONE®), (yara yara, geranium oil, rose oil, lavender oil, ylang oil, and combinations thereof.

Non-limiting examples of suitable fruity compounds include aldehyde C-16, allyl caproate, allyl cyclohexyl propionate, allyl heptanoate, amyl acetate, benzaldehyde, CASSIS®, L-citronellyl acetate, L-citronellyl nitrile, 3a,4,5,6,7,7a-hexahydro-4,7-methano-1h-inden-5 (or 6)-yl acetate (CYCLACET®), 3a,4,5,6,7,7a-hexahydro-1H-4,7-methanoinden-1-yl propanoate (CYCLAPROP®), damascenone, beta-decalactone, gamma-decalactone, diethyl malonate, dimethyl benzyl carbinol acetate, dimethyl benzyl carbinyl butyrate, dimethyl phenyl ethyl carbinol, dimethyl sulfide, γ-dodecalactone, ethyl acetate, ethyl butyrate, ethyl caproate, ethyl decadienotate, ethyl heptoate, ethyl-2-methylbutyrate, ethyl acetoacetate, ethyl methyl phenyl glycidate, ethyl propionate, 4-methyl-2-(2-methylpropyl) oxan-4-ol (FLOROL®), ethyl tricyclo [5.2.1.02.6]decan-2 carboxylate (FRUITATE®), hexyl acetate, hexyl isobutyrate, isoamyl acetate, 6-(pent-3-en-1-yl)tetrahydro-2H-pyran-2-one (Jasmolactone), ethyl 2-methylpentanoate (manzanate), 2,6-dimethylhept-5-enal (melonal), methyl anthranilate, methyl dioxolan, methyl heptyl ketone, gamma-nonalactone, 6-nonenol, gamma-octalactone, phenyl ethyl isobutyrate, prenyl acetate, raspberry ketone, methyl (2-((4S)-4-methyl-2-methylenecyclohexyl) propan-2-yl) sulfane (RINGONOL®), (1R, 6S)-ethyl 2,2,6-trimethylclocloxehanecarboxylate (THESARON®), tolyl aldehyde, γ-undecalactone, 3,5,5-trimethylhexyl acetate (vanoris), (2-tert-butylcyclohexyl)acetate (verdox), nopyl acetate, and combinations thereof.

Non-limiting examples of suitable gourmand compounds include angelica lactone-alpha, caprylic acid, coumarin, ethyl fraison, ethyl vanillin, ethyl maltol (e.g., VELTOL PLUS), filbertone, 4-hydroxy-2,5-dimethyl-3 (2H)-furanone (FURANEOL®), guaiacol, maple furanone, 2-acetyl pyrazine, 2,5-dimethyl pyrazine, cyclohex-3-en-1-ylmethyl-2-hydroxypropanoate, vanillin and combinations thereof.

Non-limiting examples of suitable green compounds include allyl amyl glycolate, cyclogalbanate, 1-(5,5-dimethyl-1-cyclohexen-1-yl)-4-Penten-1-one (DYNASCONE®), galbanolene, galbanum, trans-2-hexenal, cis-3-hexenol, hexen-1-ol, cis-3-hexenyl acetate, cis-3-hexenyl butyrate, cis-3-hexenyl formate, cis-3-hexenyl salicyclate, liffarome, 2-methoxy-2-methylheptane, methyl octine carbonate, neofolione, 2,6-nonadienal, (2R,4S)-2-methyl-4-propyl-1,3-oxathiane (OXANE®), octahydro-5-methoxy-4,7-methano-1H-indene-2-carboxaldehyde (SCENTENAL®), N-(5-methylheptan-3-ylidene) hydroxylamine (STEMONE®), styrallyl acetate, 2,4-dimethylcyclohex-3-ene-1-carbaldehyde (TRIPLAL®), undecavertol, vionil, violet methyl carbonate (e.g., VIOLET T), violet leaf extract, and combinations thereof.

Non-limiting examples of suitable herbaceous compounds include bamboo ketone, canthoxal, carvacrol, clary sage natural oil, cymene, p., 2,6-dimethylheptan-2-ol (DI-METOL®), menthol, methyl salicylate, thymol, natural basil oil, natural eucalyptus oil, eucalyptol, sweet natural fennel oil, natural cedar leaf oil, and combinations thereof.

Non-limiting examples of suitable marine compounds include 8-methyl-1,5-benzodioxepin-3-one (Calone® 1951), 3-(4-ethylphenyl)-2,2-dimethylpropanal (floralozone), 4-tert-butylphenylacetonitrile (MARENIL®), 4-[(3E)-4,8-dimethylnona-3,7-dienyl]pyridine (MARITIMA®), myrac aldehyde, ultrazure, and combinations thereof.

Non-limiting examples of suitable mossy compound include hinokitiol, isobutyl quinolone, isopropyl quinolone and/or methyl 2,4-dihydroxy-3,6-dimethylbenzoate (oakmoss® #1), and combinations thereof.

Non-limiting examples of suitable musk compounds include 17-oxacycloheptadec-6-en-1-one (ambrettolide), 5-Cyclohexadecen-1-one (AMBRETONE®), (3aR,5aS,9aS,9bR)-3a,6,6,9a-Tetramethyldodecahydronaphtho [2,1-b]furan (AMBROXAN), 2,2,6-trimethyl-alpha-propylcyclohexanepropanol (Dextramber), 16-oxacyclohexadecan-1-one (EXALTOLIDE®), 4,6,6,7,8,8-hexamethyl-1,3,4,6,7,8-hexahydro-cyclopenta[g]-isochromene (GALAXOLIDE®), ((12E)-1-oxacyclohexadec-12-en-2-one (habanolide), [2-[1-(3,3-dimethylcyclohexyl) ethoxy]-2-methylpropyl]propanoate (HELVETOLIDE®), (1'R)-3-methyl-5-(2,2,3-trimethylcyclopentan-1-yl)-2-pentanone, (5E)-3-methylcyclopentadec-5-en-1-one (MUSCENONE®), 1,4-dioxacycloheptadecane-5,17-dione (Musk T), 3-methylcyclopentadecan-1-one (L-muscone), 1-(1,1,2,6-tetramethyl-3-propan-2-yl-2,3-dihydroinden-5-yl) ethanone (TRASEOLIDE™), 1-(3,5,5,6,8,8-hexamethyl-6,7-dihydronaphthalen-2-yl) ethenone (TONALID®), and combinations thereof.

Non-limiting examples of suitable piney compounds include 1-borneol, 1-bornyl acetate, camphene, camphor gum powder, dihydroterpineol, β-pinene, and combinations thereof.

Non-limiting examples of suitable powdery compounds include heliotropine and/or whiskey lactone (methyl octalactone).

Non-limiting examples of suitable spicy compounds include acetyl isoeugenol, delta-caryophellene, cinnamaldehyde, cuminaldehyde, eugenol, isoeugenol, perilla aldehyde, cardamom oil, clove oil, ginger extract, black pepper extract and combinations thereof.

Non-limiting examples of suitable woody and/or amber compounds include amber core, amber extreme, ambretol, 4aR,5R,7aS,9R)-Octahydro-2,2,5,8,8,9a-hexamethyl-4H-4a,9-methanoazuleno[5,6-d]-1,3-dioxole (AMBROCENIDE®), ((3aR,5aS,9aS,9bR)-3a,6,6,9a-Tetramethyldodecahydronaphtho [2,1-b]furan (AMBROXAN), 2-ethyl-4-(2,2,3-trimethyl-3-cyclo-penten-1-yl)-2-buten-1-ol (BACDANOL®), ethoxymethoxycyclododecane (Boisambrene Forte), 1,1,2,3,3-pentamethyl-2,5,6,7-tetrahydroinden-4-one (Cashmeran®), ((2R,5S,7R,8R)-8-methoxy-2,6,6,8-tetramethyltricyclo [5.3.1.01,5]undecane (Cedramber®), cedanol, cedarwood oil, (1S,2R,5S,7R,8R)-2,6,6,8-tetramethyltricyclo [5.3.1.01,5]undecan-8-ol (Cedrol), 2,2,6-trimethyl-alpha-propylcyclohexanepropanol (Dextramber), 3-Methyl-5-(2,2,3-trimethyl-3-cyclopenten-1-yl)-4-penten-2-ol (EBANOL®), (R,E)-2-Methyl-4-(2,2,3-trimethylcyclopent-3-enyl) but-2-en-1-ol (HINDINOL®), hinokitiol, DH-ionone beta, [(1R,2S)-1-methyl-2-[[(1R,3S,5S)-1,2,2-trimethyl-3-bicyclo[3.1.0]hexanyl]methyl]cyclopropyl]methanol (JAVANOL®), 5-butan-2-yl-2-(2,4-dimethyl-1-cyclohex-3-enyl)-5-methyl-1,3-dioxane (karanal), 2,4-Dimethyl-2-(1,1,4,4-tetramethyltetralin-6-yl)-1,3-dioxolane (OKOUMAL®), 1-(1,2,3,4,5,6,7,8-octahydro-2,3,8,8-tetramethyl-2-naphthyl) ethan-1-one (ORBITONE®), 2-ethyl-4-[(1R)-2,2,3-trimethyl-3-cyclopenten-1-yl]-(2E)-buten-1-ol (LEVOSANDOL®), (4-tert-butylcyclohexyl)acetate (Vertenex®), patchouly oil, polysantol, rhubofix, sandalwood, and combinations thereof.

The amounts of total fragrance compounds in the fragrance composition can vary depending on the intended olfactory properties of the resulting fragrance composition. In certain embodiments, the amounts of total fragrance compounds in the fragrance composition can range from about 0.1 parts per thousand to about 999 parts per thousand, or from about 0.1 parts per thousand to about 990 parts per thousand, or from about 0.1 parts per thousand to about 900 parts per thousand, or from about 0.1 parts per thousand to about 800 parts per thousand, or from about 1 part per thousand to about 500 parts per thousand. In particular embodiments, the fragrance composition can include about 0.1 parts per thousand, about 1 parts per thousand, about 10 parts per thousand, about 100 parts per thousand, about 500 parts per thousand, about 800 parts per thousand, about 900 parts per thousand, or about 999 parts per thousand of additional fragrance compounds, based on the total weight of the fragrance composition. Expressed differently, in certain embodiments, the amounts of the additional fragrance compounds can be from about 0.01% to about 99.9%, or from about 0.01% to about 99%, or from about 0.01% to about 90%, or from about 0.01% to about 80%, of from about 0.1% to about 50% by weight, based on the total weight of the fragrance composition. In particular embodiments, the fragrance composition can include about 0.01%, about 0.1%, about 1%, about 10%, about 50%, about 80%, about 90%, or about 99% by weight of additional fragrance compounds, based on the total weight of the fragrance composition.

Such compositions can include at least one ingredient selected from a group consisting of a fragrance carrier and a fragrance base. Such compositions can further include at least one fragrance adjuvant.

Fragrance carriers can be a liquid or a solid and typically do not significantly alter the olfactory properties of the fragrance ingredients. Some non-limiting examples of fragrance carriers include an emulsifying system, encapsulating materials, natural or modified starches, polymers, gums, pectins, gelatinous or porous cellular materials, waxes, and solvents which are typically employed in fragrance applications.

Fragrance base refers to any composition comprising at least one fragrance co-ingredient. In general, these co-ingredients belong to chemical classes such as, but not limited to: alcohols, aldehydes, ketones, esters, ethers, acetals, oximes, acetates, nitriles, terpenes, saturated and unsaturated hydrocarbons, and essential oils of natural or synthetic origins.

The fragrance compositions according to the disclosed subject matter can be in the form of a simple mixture of the various co-ingredients and solvents, or also in the form of a biphasic system such as an emulsion or microemulsion. Such systems are well-known to persons skilled in the art.

Nonlimiting examples of such solvents used in perfumery are known in the art and include but are not limited to: dipropylene glycol (DPG), diethyl phthalate, isopropyl myristate, benzyl benzoate, 2-(2ethoxy)-1-ethanol, ethyl citrate, triethyl citrate (TEC), ethanol, water/ethanol mixtures, limonene or other terpenes, isoparaffins such as those known under the trademark Isopar® (ExxonMobil Chemicals, Houston, TX), and glycol ethers and glycol ether esters such as those known under the trademark Dowanol® (Dow Chemical Company, Midland MI). In particular embodiments, the solvents can include dipropylene glycol (DPG). In alternate embodiments, the solvents can include dipropylene glycol (DPG) and triethyl citrate (TEC).

4. Use of Fragrance Compositions in Consumer Products

In certain embodiments, the compositions of the present disclosure are formulated as part of a consumer product. Such consumer products can be prepared in any suitable form by any process chosen by the formulator. Suitable consumer products that can include a compound(s) of the presently disclosed subject matter include, but are not limited to, air care products (e.g., candles, aerosols, air fresheners, room sprays and mists, liquid electric air fresheners, fragrance diffusers, gel air fresheners, plug-in air fresheners and oils, wax melts, etc.); baby care products (e.g., consumer products relating to disposable absorbent and/or non-absorbent articles, including adult incontinence garments, bibs, diapers, training pants, infant and toddler care wipes; and personal care products including hand soaps, shampoos, lotions, shower gels, and clothing); fabric and home care products (e.g., consumer products for fabric conditioning (including softening), laundry detergency, laundry and rinse additive and/or care, bleach, dryer sheets, perfume beads, dishwashing, hard surface cleaning and/or treatment, and other cleaning for consumer and or institutional use, etc.); personal care products (e.g., lotions, creams, moisturizers, body washes, hand soaps, shampoos, conditioners, soaps, etc.); family care products (e.g., wet or dry bath tissue, facial tissue, disposable handkerchiefs, disposable towels, and/or wipes, towels, toilet paper, tissue paper, wet towels, etc.); feminine care products (e.g., catamenial pads, incontinence pads, interlabial pads, panty liners, pessaries, sanitary napkins, tampons and tampon applicators, and/or wipes, etc.); sexual health care products (e.g., products relating to sexual aids or sexual health, including lubricants and condoms, etc.); pet care products (e.g., pet malodor cat litter, pet deodorizers, pet health and nutrition including pet foods, treats, other orally deliverable products, grooming aids, products for treating pet hair/fur including shampooing, styling, conditioning; deodorants and antiperspirants; products for cleansing or treating pet skin, including soaps, creams, lotions, and other topically applied products; training aids, toys and diagnostics techniques); fine fragrance (e.g. hydro alcoholic solutions of perfume oil, such as parfum, extrait de parfum, eau de parfum, parfum de toilette, eau de toilette, eau de cologne, body splash, after shave, body mists, including baby colognes); auto care products (e.g., cleaners, air fresheners, wipes, soaps, etc.); cosmetics (e.g., skin cream, cleansing cream, night cream, hand cream, lotion, after-shave lotion, body lotion, foundation, lip stick, lip cream, nail polish, nail polish remover, talcum powder, anti-wrinkle and/or anti-aging cosmetics, sun protection products, massage oil, etc.); beauty care (e.g., products for treating human hair including shampooing, styling, conditioning; deodorants and antiperspirants; products for personal cleansing; products for treating human skin, including application of creams, lotions, and other topically applied products; products for shaving, rinse, rinse in shampoo; hair styling agents such as pomade, hair tonic, hair gel, hair cream and hair mousse; hair growing agents; hair coloring agents, etc.); and bath agents (e.g., powder bath additives, solid foaming bath additives, bath oils, bubble bath aroma generators, bath salts, etc.); hair removal products (e.g., products for hair removal including depilatory creams, sugar pastes or gels, waxes); and topical pharmaceuticals (e.g., ointments, creams, and the like used in the treatment and/or prevention of diseases and/or alleviation of symptoms in humans and/or animals). Depending on the solvents that can be present in some end products, it can be necessary to protect the compounds from premature degradation, for example by encapsulation or with a stabilizer, or other methods well-known to those of ordinary skill in the art.

In certain embodiments of the present disclosure, the fragrance composition can be admixed with a consumer product wherein the composition is present in an amount from about 0.0001% to about 90% by weight, or from about 0.001% to about 75% by weight, or from about 1% to about 50% by weight, or from about 5% to about 25% by weight, or from about 10% to about 15% by weight, and values in between, based on the total weight of the consumer product. In other embodiments, the fragrance composition can be admixed with a consumer product wherein the composition is present in an amount from about 0.0001% to about 10% by weight, or from about 0.001% to about 5% by weight, or from about 0.001% to about 1% by weight.

In other embodiments, the consumer product can be such that it comprises from about 90% to about 100% by weight, or from about 95% to about 100% by weight, or from about 99% to about 100% by weight of the fragrance composition, based on the total weight of the consumer product. In particular embodiments, the consumer product can be such that it comprises about 90%, about 95%, about 99%, or about 100% by weight of the fragrance composition, based on the total weight of the consumer product.

In certain embodiments, the consumer product can additionally include one or more bases, solvents, and combinations thereof. A base, as used herein, includes a composition for use in a consumer product to fulfill the specific purpose of the consumer product, such as cleaning, softening, caring, or the like.

In still other embodiments, consumer product bases and/or solvents can include, but are not limited to, essential oils, lactones, aldehydes, alcohols, ketones, nitriles, esters, terpenes, ethers, acetates, acetals, amides, oximes, and additional fragrance ingredients or fragrances.

In some embodiments, the presently disclosed compound(s) can be employed in a consumer product base simply by directly mixing at least one of the presently disclosed compound(s), or a fragrance composition comprising at least one of the presently disclosed compound(s), with the consumer product base, or the presently disclosed compound(s) can, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or it can be chemically bonded to substrates, which are adapted to release the fragrance molecule upon application of an external stimulus such as light, enzymes, or the like, and then mixed with the consumer product base.

In certain embodiments, the fragrance compounds of the present disclosure can be admixed with a consumer product wherein the disclosed fragrance compounds are present in amounts from about 0.00001% to about 20% by weight, from about 0.0001% to about 10% by weight, from about 0.001% to about 5% by weight, from about 0.01% to about 3%, by weight, and from about 0.001% to about 5% by weight, and values in between, based on the total weight of the consumer product. In particular embodiments, the fragrance compounds of the present disclosure can be admixed with a consumer product wherein the disclosed fragrance compounds are present in an amount of at least about 0.00001% by weight, at least about 0.001% by weight, at least about 5% by weight, or at least about 10% by weight, based on the total weight of the consumer product.

5. Flavor Compositions

In certain embodiments, the presently disclosed compounds can be provided in a flavor composition. Certain embodiments of the presently disclosed subject matter provide a method to modify, enhance, or improve the taste properties of a flavor composition by adding to the flavor composition an effective quantity of the presently disclosed compound.

Those skilled in the art are able to employ the desired level of said compounds to provide the desired flavor and intensity. Much higher concentrations can be employed when the compounds are used in concentrated flavors and flavor compositions. For flavor applications, concentrations of the compounds of Formulas I-III are based on the total weight of the composition into which the compound is incorporated. For flavor applications, typical concentrations of the compounds of Formula I-III can range from about 0.00001% to about 20% by weight, or from about 0.0001% to about 5% by weight, or from about 0.001% to about 3% by weight, or from about to 0.005% to about 1% by weight, based on the total weight of the composition into which the compound is incorporated. Those skilled in the art are able to employ the desired level of said compounds to provide the desired flavor and intensity. Much higher concentrations can be employed when the compounds are used in concentrated flavors and flavor compositions.

The compounds of the presently disclosed subject matter can be employed in more complex flavor compositions comprising one or more other flavor ingredients, or other flavor compositions, to modify the overall taste characteristics of the flavor composition via its own organoleptic properties or through enhancing or complimenting the contributions of the other flavor ingredient(s) present within the said composition. Such other flavor ingredients or flavor compositions include, for example, natural or synthetic flavors, i.e., fruit flavors (e.g., lemon, lime, orange, grapefruit; cherry, strawberry, raspberry, cranberry; apple, grape, pineapple, banana, tomato); natural or synthetic botanical flavors (e.g., tea flavors, coffee flavors, hazelnut, almond, pecan or other nut flavors; vanilla flavors), and flavor compositions with complex flavor profiles (e.g., cola flavors or imagined flavors, such as "birthday cake" or "ice cream sundae"). The quantity of the presently disclosed compound in such more complex flavor compositions will vary widely depending on the presence of other ingredients present, their relative amounts, the desired taste profile, and the nature of the consumer product in which the flavor composition will be utilized.

The flavor carrier can be a liquid or a solid, and typically does not significantly alter the olfactory or organoleptic properties of the flavor ingredients, respectively. Some non-limiting examples of flavor carriers include an emulsifying system, encapsulating materials, natural or modified starches, polymers, pectins, proteins, polysaccharides, gums and solvents which are typically employed in flavor applications.

The flavor compositions according to the disclosed subject matter can be in the form of a simple mixture of the various co-ingredients, adjuvants, and solvents, or also in the form of a biphasic system such as an emulsion or microemulsion. Such systems are well-known to persons skilled in the art.

The flavor compositions of the presently disclosed subject matter can further comprise one or more support materials. By way of non-limiting example, support materials can include diluents, e.g., ethanol, purified water, glycerol; solvents; carriers, e.g., propylene glycol, triacetin; preservatives, e.g., sulfites, sodium nitrite, propionic acid, sorbic acid, benzoic acid, disodium ethylenediaminetetraacetic acid (EDTA); flavoring agents, e.g., alcohols, esters, aldehydes; ketones, lactones, phenols, flavor enhancers, e.g., monosodium glutamate (MSG), monopotassium glutamate, calcium diglutamate (CDG), guanosine monophosphate disodium guanylate, sodium guanylate, inosinic acid and its salts, L-leucine; antioxidants, e.g., ascorbic acid, sodium ascorbate, fatty acid esters of ascorbic acid, tocopherols, alpha-tocopherol, gamma-tocopherol, delta-tocopherol, propyl gallate, octyl gallate, erythorbic acid, sodium erythorbate, dodecyl gallate, tertiary-butyl hydroquinone (TBHQ), butylated hydroxyanisole (BHA), butylated hydroxytoluene (BHT), citric acid, 4-hexylresorcinol; color retention agents; dyes or lakes; sequestrants, emulsifiers, e.g., lecithins, monoglyceride, acetylated monoglyceride, lactylated monoglyceride, sugar ester, sorbitan ester, polyglycerol ester, calcium stearoyl dilactylate; stabilizers; acids, bases, and/or anticaking agents, e.g., calcium silicate, magnesium carbonate, sodium aluminosilicate. Nonlimiting examples of solvents commonly used in flavors are also known in the art and include, but are not limited to: water, medium-chain triglycerides (MCTs), propylene glycol, triacetin, triethyl citrate, benzyl alcohol, benzyl benzoate, ethanol, vegetable oils, and terpenes.

The presently disclosed compounds or flavor compositions of the presently disclosed subject matter can be used in consumer products such as foods or beverages, oral care products, animal feed and pet foods, and pharmaceuticals (including over-the-counter medications). Examples of suitable consumer products include, but are not limited to carbonated fruit beverages, carbonated cola drinks, wine coolers, cordials, flavored water, powders for drinks (e.g., powdered sports or "hydrating" drinks), fruit based "smoothie" drinks, milk-based drinks, hard candy, soft candy, taffy, chocolates, sugarless candies, chewing gum, bubble gum, condiments, spices and seasonings, dry cereal, oatmeal, granola bars, condiments and preserves, soups, alcoholic beverages, energy beverages, juices, teas, coffees, salsa, gel beads, film strips for halitosis, gelatin candies, pectin candies, starch candies, lozenges, chewable tablets, breath mints, oral wash, tooth gel, cough drops, throat lozenges, throat sprays, toothpastes, mouth rinses, nicotine gums, decongestants, oral analgesics, indigestion preparations, and antacids.

The flavor compositions according to the disclosed subject matter can be in the form of a simple mixture of flavoring ingredients or in an encapsulated form, e.g., a flavoring composition entrapped into a solid matrix that can comprise wall-forming and plasticizing materials such as mono-, di-, or trisaccharides, natural or modified starches, hydrocolloids, cellulose derivatives, polyvinyl acetates, polyvinylalcohols, proteins, or pectins. Examples of particularly useful matrix materials include, for example, sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives, gelatin, agar, alginate, and mixtures thereof. Encapsulation is well-known to persons skilled in the art, and can be performed, for instance, using techniques such as spray-drying, agglomeration or extrusion, or coating encapsulation, including coacervation and complex coacervation techniques.

In one embodiment, compounds of the presently disclosed subject matter are included/used in chewing and bubble gums and confectionaries (e.g., hard or soft candies or lozenges). Chewing gum compositions typically include one or more gum bases and other standard components such as flavoring agents, softeners, sweeteners, and the like. Flavoring agents for use in chewing gum compositions are well known and include natural flavors such as citrus oils, peppermint oil, spearmint oil, oil of wintergreen, natural menthol, cinnamon, ginger, and the like; and artificial flavors such as menthol, carvone, limonene, cinnamic aldehyde, linalool, geraniol, ethyl butyrate, and the like. As is known in the art, the ingredients used in chewing gum compositions can include sweeteners, both natural and artificial and both sugar and sugarless. Sweeteners are typically present in the chewing gum compositions in amounts of from about 20% to 80% by weight, or from about 30% to 60% by weight, based on the total weight of the chewing gum composition. Sugarless sweeteners include, but are not limited sugar alcohols such as Sorbitol, manifold, xylitol, hydrogenated starch hydrolysates, malitol, and the like. High intensity sweeteners such as sucralose, aspartame, neotame, salts of acesulfame, and the like, when employed, are typically present up to about 1.0% by weight.

In an alternative embodiment, the presently disclosed compounds are included in an oral personal care product (e.g., a mouthwash or toothpaste). For example, a mouthwash can be prepared by dissolving a flavor composition (e.g., a flavor cocktail) (liquid or powder) that includes the presently disclosed compounds in a solvent (e.g., water) that further includes, for example, a flavor such as menthol and a surfactant; and then mixing the resulting solution with, for example, an aqueous erythritol solution.

In one embodiment of the presently disclosed subject matter, the presently disclosed compounds are added, directly or indirectly, to a pharmaceutical dosage form (e.g., a tablet, capsule, drop, or lozenge) that contains a therapeutically active agent (e.g., a medicament). For example, one embodiment of the presently disclosed subject matter provides a cough drop or lozenge containing one or more compounds of the present disclosure and, optionally, further containing menthol or other medicaments for the treatment of sore throat, coughing or other upper respiratory ailments.

The presently disclosed compounds can also be added to, for example, compositions for the preparation of: 1) carbonated or non-carbonated fruit beverages, carbonated cola drinks, wine coolers, fruit liquors, cordials, milk drinks, smoothie drinks, flavored water, tropical alcoholic and "virgin" drink mixes (e.g., margarita, piña colada or "rum-runner" concentrates), and powders for drinks (e.g., powdered sports or "hydrating" drinks); 2) frozen confectioneries such as ice creams, sherbets, and ice-lollies; hard candies, soft candies, taffies, chocolates, and sugarless candies; 3) desserts such as jelly and pudding; 4) confectioneries such as cakes, cookies, chewing gums, and bubble gums; 5) condiments, spices and seasonings, dry cereals, oatmeals, and granola bars; 6) alcoholic beverages, energy beverages, juices, teas, coffees, salsa, and gel beads; 7) film strips for halitosis, and oral personal care products; 8) gelatin candies, pectin candies, starch candies, lozenges, cough drops, throat lozenges, throat sprays, and toothpastes.

The presently disclosed compounds can also be added to, for example; 1) Japanese confectioneries such as buns with bean-jam filling, bars of sweet jellied bean paste, and sweet jellied pounded rice; 2) jams; candies; 3) breads; 4) beverages such as green tea, oolong tea, black tea, persimmon leaf tea, Chamomile tea, Sasa veitchii tea, mulberry leaf tea, Houttuynia cordata tea, Puer tea, Mate tea, Rooibos tea, Gimunema tea, Guava tea, coffee, espresso, and hot and cold espresso and coffee products obtained by mixing espresso and/or coffee with milk, water or other liquids suitable for oral consumption (e.g., lattes, cafe au lait, cafe mocha), and cocoa; 5) soups such as Japanese flavor soup, western flavor soup, and Chinese flavor soup; 6) seasonings; 7) various instant beverages and foods; 8) various snack foods; and 9) other compositions for oral use.

EXAMPLES

The present application is further described by means of the examples, presented below, wherein the abbreviations have the usual meaning in the art.

The use of such examples is illustrative only and does not limit the scope and meaning of the disclosed subject matter or of any exemplified term. Likewise, the disclosed subject matter is not limited to any particular preferred embodiments described herein. Indeed, many modifications and variations of the disclosed subject matter are apparent to those skilled in the art upon reading this specification. The disclosed subject matter is therefore to be limited only by the terms of the appended claims along with the full scope of equivalents to which the claims are entitled.

The following Examples are provided as specific embodiments of the present disclosure, wherein the abbreviations have the usual meaning in the art. The temperatures are indicated in degrees centigrade (° C.); the NMR spectral data were recorded in $CDCl_3$ with a 400 MHz machine for $^1H$ and $^{13}C$, the chemical displacements are indicated in ppm with respect to TMS as the standard.

EXAMPLE 1: Synthesis of 4-(cyclohex-3-en-1-yl)but-3-en-2-one

Example 1 provides a synthesis of a compound of Formula IIa, wherein X=O, $R_2$=methyl, $R_3$=$R_5$=H, and $R_6$=cyclohexenyl. This compound is an intermediate for synthesis of 4-(cyclohex-3-en-1-yl) but-3-en-2-ol and 4-(cyclohex-3-en-1-yl) but-3-en-2-yl acetate as described in Example 2 and Example 3 below.

Cyclohex-3-ene-1-carbaldehyde (70 g, 1 eq.), acetone (95.2 mL), 1% NaOH (aq.) (154 mL) and water (126 mL) were combined in a round bottom flask and heated at 70° C. for 4 hours. The mixture was subsequently cooled to room temperature, and additional 100 ml of water was added. The reaction mixture was extracted with ethyl acetate, dried over $MgSO_4$, filtered and concentrated to obtain 97 g of crude oil. The oil was distilled (0.07 T, 51° C.) to afford 69.6 g of 4-(cyclohex-3-en-1-yl) but-3-en-2-one (72.9% yield).

EXAMPLE 2: Synthesis of 4-(cyclohex-3-en-1-yl) but-3-en-2-ol

Example 2 provides a synthesis of a compound of Formula Ia, wherein $R_1$=$R_2$=$R_3$=$R_5$=H, $R_4$-methyl, $R_6$-cyclohexenyl.

A mixture of 4-(cyclohex-3-en-1-yl) but-3-en-2-one (65 g, 1 eq.) in anhydrous diethyl ether (130 mL) was added dropwise to lithium aluminum hydride (2M in THF, 125.6 mL, 0.58 eq.) under a blanket of $N_2$. The reaction temperature throughout the addition was kept below 40° C. The reaction mixture was subsequently stirred for 18 hours at room temperature. The reaction was then cooled to 10° C. on a bath of ice and NaCl and quenched slowly with water. The resulting precipitate was filtered and washed with diethyl ether. The filtrate was concentrated to give 60.9 g crude 4-(cyclohex-3-en-1-yl) but-3-en-2-ol (92.5% yield). Odor: vanilla, fresh sliced mushrooms, sweet, caramel.

EXAMPLE 3: Synthesis of 4-(cyclohex-3-en-1-yl) but-3-en-2-yl acetate

Example 3 provides a synthesis of a compound of Formula Ia, wherein $R_1$=C(O)$R_7$, $R_2$=$R_7$=methyl, $R_3$=$R_4$=$R_5$=H, and $R_6$-cyclohexenyl.

4-(cyclohex-3-en-1-yl) but-3-en-2-ol (60.9 g, 1 eq.) was combined with acetic anhydride (49.2 mL, 1.3 eq.) and toluene (60 mL) and refluxed for 24 hours. The reaction mixture was then cooled to room temperature, quenched with water, extracted with diethyl ether, and washed first with saturated $NaHCO_3$ solution, and then with brine. The organic extracts were dried over $MgSO_4$, filtered and concentrated to obtain 89.1 g of crude product. Fractional distillation provided 71.8 g of 4-(cyclohex-3-en-1-yl) but-3-en-2-yl acetate (92.4% yield). Odor: citrus, mandarin, marine. GC/MS (EI): m/z (%) 194 (1), 152 (2), 135 (3), 134 (13), 119 (10), 105 (7), 98 (6), 91 (18), 79 (46), 71 (11), 55 (10), 43 (100). $^1$H NMR ($CDCl_3$): δ 1.28 (d, 3H), 1.77 (m, 2H), 2.03 (m, 4H), 2.19 (s, 3H), 2.23 (m, 1H), 5.30 (t, 1H), 5.44 (m, 2H), 5.67 (m, 2H). $^{13}$C NMR ($CDCl_3$): δ 20.4, 21.5, 24.7, 28.4, 31.0, 36.1, 71.2, 125.9, 126.9, 127.6, 137.8, 170.4.

EXAMPLE 4: Synthesis of 4-(3-methoxybut-1-en-1-yl)cyclohex-1-ene

Example 4 provides a synthesis of a compound of Formula Ia, wherein $R_1$=$R_2$=methyl, $R_3$=$R_4$=$R_5$=H, and $R_6$=cyclohexenyl.

4-(cyclohex-3-en-1-yl) but-3-en-2-ol (1 g, 1 eq.) was added to a mixture of KHMDS (1M in THF, 7.2 mL, 1.1 eq.) and 20 mL THF while heating to 70° C. After 2 hours, iodomethane was added and the reaction mixture was stirred for 1 hour at 70° C. The reaction mixture was then cooled to room temperature, quenched with water, extracted with diethyl ether, dried over $MgSO_4$, filtered and concentrated under vacuum. The crude product was purified by Kugelrohr distillation to afford 0.62 g of 4-(3-methoxybut-1-en-1-yl) cyclohex-1-ene (56.8% yield). Odor: weak. GC/MS (EI): m/z (%) 166 (4), 151 (6), 134 (16), 123 (14), 119 (16), 111 (15), 105 (16), 97 (62), 91 (59), 85 (100), 79 (89), 71 (90), 67 (43), 59 (59), 55 (66), 41 (90).

EXAMPLE 5: Synthesis of 4-(cyclohex-3-en-1-yl)-2-methylbut-3-en-2-ol

Example 5 provides a synthesis of a compound of Formula Ia, wherein $R_1$=$R_3$=$R_5$=H, $R_2$=$R_4$-methyl, and $R_6$=cyclohexenyl.

A solution of 4-(cyclohex-3-en-1-yl) but-3-en-2-one (1 g, 1 eq.) in 2 mL of anhydrous diethyl ether was added dropwise to methyl magnesium bromide (3M in diethyl ether, 2 mL, 1.2 eq.) under a blanket of $N_2$ gas at room temperature. The reaction mixture was stirred for 12 hours, after which the reaction mixture was cooled in an ice bath and quenched with saturated $NH_4Cl$. The reaction mixture was then filtered and concentrated under vacuum. The concentrated filtrate was then purified by Kugelrohr distillation (0.4 T, 80° C.) to afford 0.74 g of 4-(cyclohex-3-en-1-yl)-2-methylbut-3-en-2-ol (67.3% yield). Odor: fresh, floral, freesia. GC/MS (EI): m/z (%) 166 (1), 151 (14), 133 (7), 122 (4), 107 (3), 97 (21), 85 (22), 71 (76), 59 (24), 43 (100).

EXAMPLE 6: Synthesis of 1-(cyclohex-3-en-1-yl)-3-methylpent-1-en-3-ol

Example 6 provides a synthesis of a compound of Formula Ia, wherein $R_1$=$R_3$=$R_5$=H, $R_2$=methyl, $R_4$=ethyl, and $R_6$=cyclohexenyl.

The same synthesis protocol as detailed in Example 5 was followed, by substituting ethyl magnesium bromide (3M in diethyl ether) for methyl magnesium bromide. 1-(cyclohex-3-en-1-yl)-3-methylpent-1-en-3-ol was isolated in 65.0% yield. Odor: strong, peppery, fresh, masculine, aromatic, herbal. GC/MS (EI): m/z (%) 180 (1), 162 (3), 151 (31), 133 (5), 119 (1), 105 (4), 93 (14), 81 (18), 71 (100), 55 (13), 43 (52).

EXAMPLE 7: Synthesis of 1-(cyclohex-3-en-1-yl)-3-methylpenta-1,4-dien-3-ol

Example 7 provides a synthesis of a compound of Formula Ia, wherein $R_1$=$R_3$=$R_5$=H, $R_2$=methyl, $R_4$=vinyl, and $R_6$=cyclohexenyl.

The same synthesis protocol as detailed in Example 5 was followed, by substituting vinyl magnesium bromide (1M in THF) for methyl magnesium bromide. 1-(cyclohex-3-en-1-yl)-3-methylpenta-1,4-dien-3-ol was isolated in 17.8% yield. Odor: milky, sweet, balsamic, vegetal, gourmand, floral, orchid. GC/MS (EI): m/z (%) 178 (1), 160 (2), 145 (2), 131 (3), 120 (5), 104 (12), 91 (32), 79 (44), 71 (21), 55 (27), 43 (100).

EXAMPLE 8: Synthesis of 1-(cyclohex-3-en-1-yl)-3,4-dimethylpent-1-en-3-ol

Example 8 provides a synthesis of a compound of Formula Ia, wherein $R_1$=$R_3$=$R_5$=H, $R_2$=methyl, $R_4$=isopropyl, and $R_6$-cyclohexenyl.

The same synthesis protocol as detailed in Example 5 was followed, by substituting isopropyl magnesium bromide (2M in THF) for methyl magnesium bromide. 1-(cyclohex-3-en-1-yl)-3,4-dimethylpent-1-en-3-ol was isolated in 19.4% yield. Odor: strong, shoe leather, slightly mossy. GC/MS (EI): m/z (%) 194 (1), 176 (2), 161 (1), 151 (4), 133 (6), 121 (5), 113 (15), 107 (5), 97 (2), 91 (8), 79 (20), 71 (21), 55 (10), 43 (100).

EXAMPLE 9: Synthesis of 1-(cyclohex-3-en-1-yl)-3-methylhex-1-en-3-ol

Example 9 provides a synthesis of a compound of Formula Ia, wherein $R_1=R_3=R_5=H$, $R_2$-methyl, $R_4$=propyl, and $R_6$=cyclohexenyl.

The same synthesis protocol as detailed in Example 5 was followed, by substituting propyl magnesium chloride (1M in 2-methyl-THF) for methyl magnesium bromide. 1-(cyclohex-3-en-1-yl)-3-methylhex-1-en-3-ol was isolated in 53.5% yield. Odor: salty, mossy, bitter grapefruit.

EXAMPLE 10: Synthesis of 4-(cyclohex-3-en-1-yl) but-3-en-2-one oxime

Example 10 provides a synthesis of a compound of Formula IIa, wherein X=NOH, $R_2$-methyl, $R_3$-$R_5$=H, $R_6$-cyclohexenyl.

4-(cyclohex-3-en-1-yl) but-3-en-2-one (1 g, 1 eq.) was added to a mixture of hydroxylamine-HCl (0.78 g, 1.7 eq.), 20 mL ethanol and pyridine (1.08 mL, 2 eq.) under a blanket of $N_2$ gas. The reaction mixture was heated to 90° C. for 18 hours. After cooling the reaction mixture to room temperature, the ethanol was removed under vacuum. The remaining mixture was quenched with water, extracted with ethyl acetate and washed first with 1N HCl and then with brine. The extract was dried over $MgSO_4$, filtered and concentrated to a thick yellow oil. The crude product was purified by Kugelrohr distillation (0.35 T, up to 100° C.) to afford 0.14 g of 4-(cyclohex-3-en-1-yl) but-3-en-2-one oxime (12.5% yield). Odor: weak.

EXAMPLE 11: Synthesis of 4-(cyclohex-3-en-1-yl) but-3-en-2-one O-methyl oxime Example 11 provides a synthesis of a compound shown in Formula IIa, wherein X=NOCH$_3$, $R_2$=methyl, $R_3$-$R_5$=H, $R_6$=cyclohexenyl.

The same synthesis protocol as detailed in Example 10 was followed, by substituting O-methyl hydroxylamine-HCl for hydroxylamine-HCl. 4-(cyclohex-3-en-1-yl) but-3-en-2-one O-methyl oxime was isolated in 50.0% yield. Odor: licorice, aldehydic, floral, green. GC/MS (EI): m/z (%) 179 (5), 164 (3), 148 (20), 132 (5), 124 (61), 118 (4), 110 (6), 105 (7), 100 (7), 94 (100), 79 (65), 70 (16), 65 (36), 53 (79), 42 (77).

EXAMPLE 12: Synthesis of 3-(cyclohex-3-en-1-yl)-2-methylacrylaldehyde

Example 12 provides a synthesis of a compound shown in Formula IIa, wherein X=O, $R_2$=$R_5$=H, $R_3$=methyl, $R_6$-cyclohexenyl.

Cyclohex-3-ene-1-carbaldehyde (20 g, 1 eq.), was added to NaOH (2.17 g,.3 eq.) and water (60 mL), and the reaction mixture was heated to 35° C. Propionaldehyde (11.6 g, 1.1 eq.) was added dropwise and the reaction mixture was subsequently heated at 80° C. for 16 hours. After this time, the reaction mixture was cooled to room temperature, an additional 100 ml of water was added, and the reaction mixture was extracted with diethyl ether, washed first with 1N HCl, then with brine, dried over $MgSO_4$, filtered and concentrated to obtain 29.5 g of crude oil. The crude product was purified by Kugelrohr distillation (0.3 T, 66° C.) to afford 13.0 g of 3-(cyclohex-3-en-1-yl)-2-methylacrylaldehyde (47.7% yield). Odor: Spicy, strong, cinnamic, wasabi, shiso.

EXAMPLE 13: Synthesis of 3-(cyclohex-3-en-1-yl)-2-methylprop-2-en-1-ol

Example 13 provides a synthesis of a compound shown in Formula Ia, wherein $R_1=R_2=R_4=R_5=H$, $R_3$-methyl, and $R_6$=cyclohexenyl.

3-(cyclohex-3-en-1-yl)-2-methylacrylaldehyde (3.9 g, 1 eq.) and 24 mL methanol were added to a flask under a blanket of $N_2$ gas and cooled to 5° C. Sodium borohydride (1.6 g, 1.2 eq.) was added and the reaction mixture was stirred at temperature below 10° C. for 2 hours. After this time, the reaction mixture was quenched while cold with water, and the methanol was removed under vacuum. The resulting mixture was extracted with ethyl acetate and concentrated. The crude product was purified by Kugelrohr distillation to afford 3.2 g of 3-(cyclohex-3-en-1-yl)-2-methylprop-2-en-1-ol (82.0% yield). Odor: very strong, muguet, rose, peony, creamy, lactonic. GC/MS (EI): m/z (%) 152.1 (M+, 1), 134.1 (2), 121.1 (1), 105.1 (1), 98.1 (7), 97.1 (6), 91.1 (3), 83.1 (7), 80.1 (6), 69.1 (6), 51.1 (1), 43.1 (6). $^1$H NMR (CDCl$_3$): 5.62-5.70 (m, 2H), 5.30 (dq, J=9.16, 1.37 Hz, 1H), 3.99 (d, J=3.66 Hz, 2H), 2.43-2.55 (m, 1H), 2.02-2.08 (m, 3H), 1.60-1.80 (m, 4H), 1.32-1.42 (m, 2H). $^{13}$C NMR (CDCl$_3$): 133.71, 131.51, 127.02, 126.30, 69.04, 32.45, 31.54, 28.77, 24.81, 13.81.

EXAMPLE 14: Synthesis of 3-(cyclohex-3-en-1-yl)-2-methylallyl acetate

Example 14 provides a synthesis of a compound shown in Formula Ia, wherein $R_1$=C(O)R$_7$, $R_2=R_4=R_5=H$, $R_3$=methyl, $R_6$=cyclohexenyl, and $R_7$-methyl.

The same synthesis protocol as detailed in Example 3 was followed, by substituting 3-(cyclohex-3-en-1-yl)-2-methylprop-2-en-1-ol for 4-(cyclohex-3-en-1-yl) but-3-en-2-ol. 3-(cyclohex-3-en-1-yl)-2-methylallyl acetate was isolated in 68.5% yield. Odor: rosy, powdery, fruity, stewed apricots, green, peony. GC/MS (EI): m/z (%) 194 (1), 152 (5), 134 (18), 119 (11), 105 (7), 91 (29), 79 (52), 67 (11), 53 (14), 43 (100).

EXAMPLE 15: Synthesis of 4-(3-methoxy-2-methylprop-1-en-1-yl)cyclohex-1-ene

Example 15 provides a synthesis of a compound shown in Formula Ia, wherein $R_1=R_3$=methyl, $R_2=R_4=R_5=H$, and $R_6$=cyclohexenyl.

The same synthesis protocol as detailed in Example 4 was followed, by substituting 3-(cyclohex-3-en-1-yl)-2-methylprop-2-en-1-ol for 4-(cyclohex-3-en-1-yl) but-3-en-2-ol. 4-(3-methoxy-2-methylprop-1-en-1-yl)cyclohex-1-ene was isolated in 46.1% yield. Odor: anisic, powdery, mildew, cypress, spicy. GC/MS (EI): m/z (%) 166 (2), 150 (9), 135 (30), 121 (6), 112 (10), 94 (29), 80 (100), 67 (46), 55 (51), 45 (100).

EXAMPLE 16: Synthesis of 4-(cyclohex-3-en-1-yl)-3-methylbut-3-en-2-ol

Example 16 provides a synthesis of a compound shown in Formula Ia, wherein $R_1=R_2=R_5=H$, $R_3=R_4$-methyl, and $R_6$=cyclohexenyl.

The same synthesis protocol as detailed in Example 5 was followed, by substituting 3-(cyclohex-3-en-1-yl)-2-methylacrylaldehyde for 4-(cyclohex-3-en-1-yl) but-3-en-2-one. 4-(cyclohex-3-en-1-yl)-3-methylbut-3-en-2-ol was isolated in 66.3% yield. Odor: Floral, aldehydic, muguet. GC/MS (EI): m/z (%) 166.1 (M+, 1), 133.1 (1), 123.1 (1), 112.1 (2), 97.1 (8), 91.1 (2), 85.1 (6), 79.1 (5), 69.1 (6), 55.1 (1), 43.1 (7). $^1$H NMR (CDCl$_3$): 5.63-5.70 (m, 2H), 5.29 (d, J=9.16 Hz, 1H), 4.18 (q, J=5.95 Hz, 1H), 2.41-2.51 (m, 1H), 1.99-2.07 (m, 3H), 1.59-1.81 (m, 4H), 1.23-1.41 (m, 5H). $^{13}$C NMR (CDCl$_3$): (diastereomer mixture) 137.50, 130.41, 130.33, 127.03, 127.00, 126.36, 126.33, 73.48, 73.45, 32.33, 31.55, 31.53, 28.76, 24.82, 21.73, 11.63, 11.55.

EXAMPLE 17: Synthesis of 1-(cyclohex-3-en-1-yl)-2-methylpent-1-en-3-ol

Example 17 provides a synthesis of a compound shown in Formula Ia, wherein $R_1=R_2=R_5=H$, $R_3$=methyl, $R_4$-ethyl, and $R_6$-cyclohexenyl.

The same synthesis protocol as detailed in Example 6 was followed, by substituting 3-(cyclohex-3-en-1-yl)-2-methylacrylaldehyde for 4-(cyclohex-3-en-1-yl) but-3-en-2-one. 1-(cyclohex-3-en-1-yl)-2-methylpent-1-en-3-ol was isolated in 74.4% yield. Odor: floral, petaly, powdery bloom, balsamic, herbal, woody, spicy, sandal, complex. GC/MS (EI): m/z (%) 180 (3), 171 (1), 162 (7), 151 (27), 133 (12), 123 (7), 115 (2), 108 (12), 97 (47), 91 (28), 81 (54), 71 (57), 57 (100), 51 (7), 41 (74). $^1$H NMR (CDCl$_3$): δ 0.82 (t, 3H), 1.3-1.81 (m, 9H, including 3H singlet), 2.04 (m, 3H), 2.47 (broad, 1H), 3.87 (t, 1H), 5.25 (d, 1H), 5.65 (m, 2H). $^{13}$C NMR (CDCl$_3$): δ 10.0, 11.0, 24.7, 27.6, 27.7, 29.0, 31.4, 79.1, 126.2, 126.3, 126.9, 132.2.

EXAMPLE 18: Synthesis of 1-(cyclohex-3-en-1-yl)-2-methylhex-1-en-3-ol

Example 18 provides a synthesis of a compound shown in Formula Ia, wherein $R_1=R_2=R_5=H$, $R_3$-methyl, $R_4$-propyl, and $R_6$=cyclohexenyl.

The same synthesis protocol as detailed in Example 9 was followed, by substituting 3-(cyclohex-3-en-1-yl)-2-methylacrylaldehyde for 4-(cyclohex-3-en-1-yl) but-3-en-2-one. 1-(cyclohex-3-en-1-yl)-2-methylhex-1-en-3-ol was isolated in 7.7% yield. GC/MS (EI): m/z (%) 194 (2), 176 (6), 161 (1), 151 (13), 133 (7), 122 (5), 113 (20), 105 (6), 93 (65), 81 (47), 71 (100), 55 (27), 41 (62).

EXAMPLE 19: Synthesis of 1-(cyclohex-3-en-1-yl)-2-methylhexa-1,5-dien-3-ol

Example 19 provides a synthesis of a compound shown in Formula Ia, wherein $R_1=R_2=R_5=H$, $R_3$-methyl, $R_4$-allyl, and $R_6$=cyclohexenyl.

The same synthesis protocol as detailed in Example 9 was followed, by substituting 3-(cyclohex-3-en-1-yl)-2-methylacrylaldehyde for 4-(cyclohex-3-en-1-yl) but-3-en-2-one. 1-(cyclohex-3-en-1-yl)-2-methylhexa-1,5-dien-3-ol was isolated in 9.4% yield. Odor: solventy, weak.

EXAMPLE 20: Synthesis of 3-(cyclohex-3-en-1-yl)-2-methylacrylaldehyde oxime

Example 20 provides a synthesis of a compound shown in Formula IIa, wherein X=NOH, $R_2=R_5$=H, $R_3$-methyl, $R_6$=cyclohexenyl.

The same synthesis protocol as detailed in Example 10 was followed, by substituting 3-(cyclohex-3-en-1-yl)-2-methylacrylaldehyde for 4-(cyclohex-3-en-1-yl) but-3-en-2-one. 3-(cyclohex-3-en-1-yl)-2-methylacrylaldehyde oxime was isolated in 54.5% yield. Odor: weak, leathery, mossy. GC/MS (EI): m/z (%) 165.1 (M+, 3), 148.1 (3), 133.1 (1), 110.1 (17), 94.1 (9), 79.1 (5), 67.1 (2), 39.1 (2).

EXAMPLE 21: Synthesis of 3-(cyclohex-3-en-1-yl)-2-methylacrylaldehyde O-methyl oxime Example 21 provides a synthesis of a compound shown in Formula IIa, wherein X=NOCH$_3$, $R_2=R_5$=H, $R_3$=methyl, $R_6$=cyclohexenyl.

The same synthesis protocol as detailed in Example 11 was followed, by substituting 3-(cyclohex-3-en-1-yl)-2-methylacrylaldehyde for 4-(cyclohex-3-en-1-yl) but-3-en-2-one. 3-(cyclohex-3-en-1-yl)-2-methylacrylaldehyde O-methyl oxime was isolated in 94.1% yield. Odor: weak, fruity, violet.

EXAMPLE 22: Synthesis of (Cyclohex-3-en-1-yl)-2-methylacrylonitrile

Example 22 provides a synthesis of a compound shown in Formula IIIa, wherein $R_3$-methyl, $R_5$=H, and $R_6$=cyclohexenyl.

3-(cyclohex-3-en-1-yl)-2-methylacrylaldehyde oxime (0.6 g, 1 eq.) was refluxed with 0.06 g K$_3$PO$_4$ (10 wt % of oxime) and 6 mL xylenes for 6 hours. After cooling, the reaction mixture was quenched with water and extracted with diethyl ether. The crude product was purified by Kugelrohr distillation to afford 0.38 g of (cyclohex-3-en-1-yl)-2-methylacrylonitrile (71.7% yield). Odor: natural honey note, balsamic, citral, lemon. GC/MS (EI): m/z (%) 179.2 (M+, 20), 164.1 (3), 148.2 (16), 124.1 (58), 110.1 (7), 94.1 (72), 80.1 (42), 67.1 (12), 50.1 (1), 41.1 (10). $^1$H NMR (CDCl$_3$): 7.63 (s, 1H), 5.64-5.69 (m, 2H), 5.57 (d, J=10.07 Hz, 1H), 3.85 (s, 3H), 2.64-2.69 (m, 1H), 2.05-2.11 (m, 3H), 1.77-1.85 (m, 4H), 1.67-1.71 (m, 1H), 1.36-1.46 (m, 1H). $^{13}$C NMR (CDCl$_3$): 153.67, 143.81, 129.60, 127.07, 125.82, 61.69, 32.99, 30.99, 28.28, 24.50, 11.67.

EXAMPLE 23: Synthesis of 2-(cyclohex-3-en-1-ylmethylene)cyclopentan-1-one

Example 23 provides a synthesis of a compound shown in Formula IIb, wherein n=1, X=O, $R_2$-$R_3$-methyl, $R_5$=H, $R_6$=cyclohexenyl.

Cyclohex-3-ene-1-carbaldehyde (20 g, 1 eq.), cyclopentanone (24 mL, 1.5 eq.), NaOH (2.18 g, 0.3 eq.) and water (60 mL) were combined and heated at 35° C. for 18 hours. After cooling to room temperature, an additional 100 ml of water was added and the reaction mixture was extracted with ethyl acetate, washed first with 1N HCl, washed then with brine, dried over MgSO$_4$, filtered and concentrated to 14.4 g crude oil. The crude product was purified by Kugelrohr distillation (0.15 T, 69° C.) to afford 8.8 g of 2-(cyclohex-3-en-1-ylmethylene)cyclopentan-1-one (27.5% yield). Odor: dill weed, tart, bright

EXAMPLE 24: Synthesis of 2-(cyclohex-3-en-1-ylmethylene)cyclopentan-1-ol

Example 24 provides a synthesis of a compound shown in Formula Ib, wherein n=1, $R_1$=$R_4$=$R_5$=H, $R_2$=$R_3$-methyl, $R_6$=cyclohexenyl.

The same synthesis protocol as detailed in Example 2 was followed, by substituting 2-(cyclohex-3-en-1-ylmethylene)cyclopentan-1-one for 4-(cyclohex-3-en-1-yl) but-3-en-2-one. 2-(cyclohex-3-en-1-ylmethylene)cyclopentan-1-ol was isolated in 74.3% yield. Odor: buttery, mothball, indole, floral. GC/MS (EI): m/z (%) 178 (3), 160 (24), 145 (2), 131 (10), 117 (16), 106 (68), 97 (79), 79 (200), 67 (47), 53 (28), 41 (52).

EXAMPLE 25: Synthesis of 2-(cyclohex-3-en-1-ylmethylene)cyclopentyl acetate

Example 25 provides a synthesis of a compound shown in Formula Ib, wherein n=1, $R_1$=C(O)$R_7$, $R_2$=$R_3$=$R_7$-methyl, $R_4$=$R_5$=H, $R_6$=cyclohexenyl.

The same synthesis protocol as detailed in Example 3 was followed, by substituting 2-(cyclohex-3-en-1-ylmethylene)cyclopentan-1-ol for 4-(cyclohex-3-en-1-yl) but-3-en-2-ol. 2-(cyclohex-3-en-1-ylmethylene)cyclopentyl acetate was isolated in 66.6% yield. Odor: strong; substantive, citrus, sulfury. GC/MS (EI): m/z (%) 220 (1), 178 (2), 160 (16), 145 (3), 131 (7), 124 (3), 117 (18), 106 (73), 97 (39), 91 (83), 79 (100), 67 (41), 53 (27), 43 (72).

EXAMPLE 26: Synthesis of 4-((2-methoxycyclopentylidene)methyl)cyclohex-1-ene Example 26 provides a synthesis of a compound shown in Formula Ib, wherein n=1, $R_1$=$R_2$=$R_3$=methyl, $R_4$=$R_5$=H, $R_6$=cyclohexenyl.

The same synthesis protocol as detailed in Example 4 was followed, by substituting 2-(cyclohex-3-en-1-ylmethylene)cyclopentan-1-ol for 4-(cyclohex-3-en-1-yl) but-3-en-2-ol. 4-((2-methoxycyclopentylidene)methyl)cyclohex-1-ene was isolated in 68.2% yield. Odor: onion, gassy.

EXAMPLE 27: Synthesis of 4-(bicyclo[2.2.1]hept-5-en-2-yl) but-3-en-2-one

Example 27 provides a synthesis of a compound shown in Formula IIa, wherein X=O, $R_2$=methyl, $R_3$=$R_5$=H, $R_6$=bicyclo[2.2.1]hept-5-enyl.

The same synthesis protocol as detailed in Example 1 was followed, by substituting bicyclo[2.2.1]hept-5-ene-2-carbaldehyde for cyclohex-3-ene-1-carbaldehyde. 4-(bicyclo[2.2.1]hept-5-en-2-yl) but-3-en-2-one was isolated in 47.7% yield. Odor: harsh, spicy.

EXAMPLE 28: Synthesis of 4-(bicyclo[2.2.1]hept-5-en-2-yl) but-3-en-2-ol

Example 28 provides a synthesis of a compound shown in Formula Ia, wherein $R_1$=$R_3$=$R_4$=$R_5$=H, $R_2$=methyl, and $R_6$-bicyclo[2.2.1]hept-5-enyl.

The same synthesis protocol as detailed in Example 2 was followed, by substituting 4-(bicyclo[2.2.1]hept-5-en-2-yl) but-3-en-2-one for 4-(cyclohex-3-en-1-yl) but-3-en-2-one. 4-(bicyclo[2.2.1]hept-5-en-2-yl) but-3-en-2-ol was isolated in 68.0% yield. Odor: slightly floral, rotting cucumber, fruity. GC/MS (EI): m/z (%) 164 (1), 148 (2), 131 (3), 120 (5), 115 (3), 105 (5), 95 (6), 91 (20), 79 (28), 66 (100), 53 (14), 45 (7), 41 (31).

EXAMPLE 29: Synthesis of 4-(bicyclo[2.2.1]hept-5-en-2-yl) but-3-en-2-yl acetate Example 29 provides a synthesis of a compound shown in Formula Ia, wherein $R_1$=C(O)$R_7$, $R_2$=$R_7$-methyl, $R_3$=$R_4$=$R_5$=H and $R_6$-bicyclo[2.2.1]hept-5-enyl.

The same synthesis protocol as detailed in Example 3 was followed, by substituting 4-(bicyclo[2.2.1]hept-5-en-2-yl) but-3-en-2-ol for 4-(cyclohex-3-en-1-yl) but-3-en-2-ol. 4-(bicyclo[2.2.1]hept-5-en-2-yl) but-3-en-2-yl acetate was isolated in 66.6% yield. Odor: wet dog, costus, marine-like, sea shore. GC/MS (EI): m/z (%) 191 ($M^+$-15, 1), 146 (8), 140 (6), 131 (8), 117 (6), 105 (3), 98 (8), 91 (12), 81 (26), 66 (65), 53 (10), 43 (100).

EXAMPLE 30: Synthesis of 5-(3-methoxybut-1-en-1-yl) bicyclo[2.2.1]hept-2-ene Example 30 provides a synthesis of a compound shown in Formula Ia, wherein $R_1$=$R_2$=methyl, $R_3$=$R_4$=$R_5$=H, and $R_6$=bicyclo[2.2.1]hept-5-enyl.

The same synthesis protocol as detailed in Example 4 was followed, by substituting 4-(bicyclo[2.2.1]hept-5-en-2-yl) but-3-en-2-ol for 4-(cyclohex-3-en-1-yl) but-3-en-2-ol. 5-(3-methoxybut-1-en-1-yl) bicyclo[2.2.1]hept-2-ene was isolated in 71.3% yield. Odor: weak, violet. GC/MS (EI): m/z (%) 178 (1), 163 (1), 146 (5), 131 (4), 117 (5), 111 (11), 105 (3), 97 (58), 91 (14), 81 (60), 66 (100), 59 (43), 53 (16), 41 (34).

EXAMPLE 31: Synthesis of 4-(bicyclo[2.2.1]hept-5-en-2-yl)-2-methylbut-3-en-2-ol Example 31 provides a synthesis of a compound shown in Formula Ia, wherein $R_1$=$R_3$=$R_5$=H, $R_2$=$R_4$-methyl, $R_6$-bicyclo[2.2.1]hept-5-enyl.

The same synthesis protocol as detailed in Example 5 was followed, by substituting 4-(bicyclo[2.2.1]hept-5-en-2-yl) but-3-en-2-one for 4-(cyclohex-3-en-1-yl) but-3-en-2-one. 4-(bicyclo[2.2.1]hept-5-en-2-yl)-2-methylbut-3-en-2-ol was isolated in 30.3% yield. Odor: weak, violet, muguet. GC/MS (EI): m/z (%) 178 (1), 160 (3), 145 (2), 128 (1), 117 (6), 111 (1), 105 (4), 95 (36), 79 (37), 66 (100), 59 (18), 53 (16), 41 (72).

EXAMPLE 32: Synthesis of 1-(bicyclo[2.2.1]hept-5-en-2-yl)-3-methylpent-1-en-3-ol Example 32 provides a synthesis of a compound shown in Formula Ia, wherein Rt=$R_3$=$R_5$=H, $R_2$-methyl, $R_4$-ethyl, and $R_6$=bicyclo[2.2.1]hept-5-enyl.

The same synthesis protocol as detailed in Example 6 was followed, by substituting 4-(bicyclo[2.2.1]hept-5-en-2-yl) but-3-en-2-one for 4-(cyclohex-3-en-1-yl) but-3-en-2-one. 1-(bicyclo[2.2.1]hept-5-en-2-yl)-3-methylpent-1-en-3-ol was isolated in 50.0% yield. Odor: wet hair, costus, sweaty, fig, liquor, fruity, smooth, violet, muguet, floral, apple, buttery, creamy. GC/MS (EI): m/z (%) 192 (1), 163 (1), 145 (1), 120 (3), 91 (15), 66 (100), 43 (67).

EXAMPLE 33: Synthesis of 1-(bicyclo[2.2.1]hept-5-en-2-yl)-3-methylpenta-1,4-dien-3-ol Example 33 provides a synthesis of a compound shown in Formula Ia, wherein $R_1=R_3=R_5=H$, $R_2$-methyl, $R_4$-vinyl, and $R_6$-bicyclo[2.2.1]hept-5-enyl.

The same synthesis protocol as detailed in Example 7 was followed, by substituting 4-(bicyclo[2.2.1]hept-5-en-2-yl) but-3-en-2-one for 4-(cyclohex-3-en-1-yl) but-3-en-2-one. 1-(bicyclo[2.2.1]hept-5-en-2-yl)-3-methylpenta-1,4-dien-3-ol was isolated in 12.5% yield. GC/MS (EI): m/z (%) 190 (1), 174 (3), 157 (2), 148 (1), 143 (2), 129 (4), 120 (2), 115 (7), 108 (26), 93 (100), 79 (59), 71 (8), 66 (90), 53 (25), 43 (67).

EXAMPLE 34: Synthesis of 1-(bicyclo[2.2.1]hept-5-en-2-yl)-3,4-dimethylpent-1-en-3-ol Example 34 provides a synthesis of a compound shown in Formula Ia, wherein $R_1=R_3=R_5=H$, $R_2$-methyl, $R_4$=isopropyl, and $R_6$=bicyclo[2.2.1]hept-5-enyl.

The same synthesis protocol as detailed in Example 8 was followed, by substituting 4-(bicyclo[2.2.1]hept-5-en-2-yl) but-3-en-2-one for 4-(cyclohex-3-en-1-yl) but-3-en-2-one. 1-(bicyclo[2.2.1]hept-5-en-2-yl)-3,4-dimethylpent-1-en-3-ol was isolated 50.0% yield. Odor: dill, blueberry, sour, medicinal.

EXAMPLE 35: Synthesis of 1-(bicyclo[2.2.1]hept-5-en-2-yl)-3-methylhex-1-en-3-ol Example 35 provides a synthesis of a compound shown in Formula Ia, wherein $R_1=R_3=R_5=H$, $R_2$=methyl, $R_4$=propyl, and $R_6$-bicyclo[2.2.1]hept-5-enyl.

The same synthesis protocol as detailed in Example 9 was followed, by substituting 4-(bicyclo[2.2.1]hept-5-en-2-yl) but-3-en-2-one for 4-(cyclohex-3-en-1-yl) but-3-en-2-one. 1-(bicyclo[2.2.1]hept-5-en-2-yl)-3-methylpenta-1,4-dien-3-ol was isolated in 44.1% yield. Odor: savory, rosemary, sage, dill, complex, mossy, violet. GC/MS (EI): m/z (%) 206 (1), 188 (1), 163 (1), 148 (3), 141 (4), 133 (1), 127 (5), 119 (2), 111 (1), 105 (2), 97 (4), 91 (6), 83 (4), 77 (6), 66 (100), 55 (10), 43 (71).

EXAMPLE 36: Synthesis of 4-(bicyclo[2.2.1]hept-5-en-2-yl) but-3-en-2-one O-methyl oxime Example 36 provides a synthesis of a compound shown in Formula IIa, wherein X=NOCH$_3$, $R_2$=methyl, $R_3=R_5=H$, and $R_6$=bicyclo[2.2.1]hept-5-enyl.

The same synthesis protocol as detailed in Example 11 was followed, by substituting 4-(bicyclo[2.2.1]hept-5-en-2-yl) but-3-en-2-one for 4-(cyclohex-3-en-1-yl) but-3-en-2-one. 4-(bicyclo[2.2.1]hept-5-en-2-yl) but-3-en-2-one O-methyl oxime was isolated in 66.1% yield. Odor: milky, vegetal, muguet. GC/MS (EI): m/z (%) 191 (1), 176 (1), 161 (4), 146 (3), 141 (4), 137 (3), 124 (70), 115 (14), 105 (6), 94 (100), 77 (35), 66 (48), 53 (31), 42 (60).

EXAMPLE 37: Synthesis of 3-(bicyclo[2.2.1]hept-5-en-2-yl)-2-methylacrylaldehyde Example 37 provides a synthesis of a compound shown in Formula IIa, wherein X=O, $R_2=R_5=H$, $R_3$-methyl, $R_6$=bicyclo[2.2.1]hept-5-enyl.

The same synthesis protocol as detailed in Example 12 was followed by substituting bicyclo[2.2.1]hept-5-ene-2-carbaldehyde for cyclohex-3-ene-1-carbaldehyde. 3-(bicyclo[2.2.1]hept-5-en-2-yl)-2-methylacrylaldehyde was isolated in 63.1% yield as a mixture with two major isomers. Odor: harsh, chemical, cheesy. $^1$H NMR (CDCl$_3$): δ 9.27 and 9.36 (singlets, 1H aldehyde peaks), 1.76 and 1.77 (singlets, 3H methyl peaks) $^{13}$C NMR (CDCl$_3$): δ 195.2 and 195.4 (aldehyde peaks).

EXAMPLE 38: Synthesis of 3-(bicyclo[2.2.1]hept-5-en-2-yl)-2-methylprop-2-en-1-ol Example 38 provides a synthesis of a compound shown in Formula Ia, wherein $R_1=R_2=R_4=R_5=H$, $R_3$-methyl, and $R_6$=bicyclo[2.2.1]hept-5-enyl.

The same synthesis protocol as detailed in Example 13 was followed, by substituting 3-(bicyclo[2.2.1]hept-5-en-2-yl)-2-methylacrylaldehyde for 3-(cyclohex-3-en-1-yl)-2-methylacrylaldehyde. 3-(bicyclo[2.2.1]hept-5-en-2-yl)-2-methylprop-2-en-1-ol was isolated in 56.15% yield. Odor: green, chemical, leafy, vegetable. GC/MS (EI): m/z (%) 164 (1), 149 (8), 138 (100), 123 (4), 101 (4), 85 (25), 73 (98), 55 (14), 41 (27).

EXAMPLE 39: Synthesis of 3-(bicyclo[2.2.1]hept-5-en-2-yl)-2-methylallyl acetate Example 39 provides a synthesis of a compound shown in Formula Ia, wherein $R_1$=C(O)$R_7$, $R_2=R_4=R_5=H$, $R_3$-methyl, $R_6$=bicyclo[2.2.1]hept-5-enyl, and $R_7$-methyl.

The same synthesis protocol as detailed in Example 14 was followed by substituting 3-(bicyclo[2.2.1]hept-5-en-2-yl)-2-methylprop-2-en-1-ol for 4-(cyclohex-3-en-1-yl) but-3-en-2-ol. 3-(bicyclo[2.2.1]hept-5-en-2-yl)-2-methylallyl acetate was isolated in 28.0% yield. Odor: gourmand, lactonic, buttery, milky, sweet.

EXAMPLE 40: Synthesis of 4-cyclohexylbut-3-en-2-one

Example 40 provides a synthesis of a compound shown in Formula IIa, wherein X=O, $R_2$-methyl, $R_3=R_5=H$, $R_6$=cyclohexyl.

The same synthesis protocol as detailed in Example 1 was followed, by substituting cyclohexanecarbaldehyde for cyclohex-3-ene-1-carbaldehyde. 4-cyclohexylbut-3-en-2-one was isolated in 65.8% yield. Odor: balsamic, herbal, peppery, cumin, pine. GC/MS (EI): m/z (%) 152 (20), 137 (6), 119 (3), 109 (23), 94 (40), 79 (28), 67 (61), 55 (76), 43 (100).

EXAMPLE 41: Synthesis of 4-cyclohexylbut-3-en-2-ol

Example 41 provides synthesis of a compound shown in Formula Ia, wherein $R_1=R_3=R_4=R_5=H$, $R_2$=methyl, and $R_6$=cyclohexyl.

The same synthesis protocol as detailed in Example 2 was followed, by substituting 4-cyclohexylbut-3-en-2-one for 4-(cyclohex-3-en-1-yl) but-3-en-2-one. 4-cyclohexylbut-3-en-2-ol was isolated in 56.4% yield. Odor: herbal, sweet, creamy, oily, paint-like. GC/MS (EI): m/z (%) 154 (1), 136 (30), 121 (20), 107 (33), 99 (27), 94 (29), 83 (17), 79 (76), 71 (100), 67 (79), 55 (75), 41 (86).

EXAMPLE 42: Synthesis of 4-cyclohexylbut-3-en-2-yl acetate

Example 42 provides synthesis of a compound shown in Formula Ia, wherein $R_1$=C(O)$R_7$, $R_2=R_7$-methyl, $R_3=R_4=R_5=H$, and $R_6$-cyclohexyl.

The same synthesis protocol as detailed in Example 3 was followed, by substituting 4-cyclohexylbut-3-en-2-ol for 4-(cyclohex-3-en-1-yl) but-3-en-2-ol. 4-cyclohexylbut-3-en-2-yl acetate was obtained in 67.7% yield. Odor: pleasant, similar to linalool acetate, citrus. GC/MS (EI): m/z (%) 196 (1), 181 (1), 154 (7), 136 (18), 121 (6), 113 (4), 107 (20), 99 (4), 93 (10), 79 (35), 67 (32), 55 (25), 43 (100).

EXAMPLE 43: Synthesis of (3-methoxybut-1-en-1-yl)cyclohexane

Example 43 provides synthesis of a compound shown in Formula Ia, wherein $R_1$=$R_2$=methyl, $R_3$=$R_4$=$R_5$=H and $R_6$=cyclohexyl.

The same synthesis protocol as detailed in Example 4 was followed, by substituting 4-cyclohexylbut-3-en-2-ol for 4-(cyclohex-3-en-1-yl) but-3-en-2-ol. (3-methoxybut-1-en-1-yl)cyclohexane was isolated in 55.0% yield. Odor: rotten, garbage. GC/MS (EI): m/z (%) 168 (1), 153 (3), 136 (5), 121 (4), 113 (4), 107 (6), 97 (2), 93 (7), 85 (100), 79 (28), 71 (58), 67 (24), 59 (30), 55 (40), 41 (45).

EXAMPLE 44: Synthesis of 4-cyclohexyl-2-methylbut-3-en-2-ol

Example 44 provides synthesis of a compound shown in Formula Ia, wherein $R_1$=$R_3$=$R_5$=H, $R_2$=$R_4$-methyl, and $R_6$=cyclohexyl.

The same synthesis protocol as detailed in Example 5 was followed, by substituting 4-cyclohexylbut-3-en-2-one for 4-(cyclohex-3-en-1-yl) but-3-en-2-one. 4-cyclohexyl-2-methylbut-3-en-2-ol was isolated in 49.0% yield. Odor: freesia, muguet, linalool-like. GC/MS (EI): m/z (%) 168 (1), 150 (14), 135 (18), 121 (3), 107 (15), 99 (16), 93 (25), 85 (39), 79 (42), 71 (100), 67 (56), 59 (25), 55 (36), 41 (83).

EXAMPLE 45: Synthesis of 1-cyclohexyl-3-methylpent-1-en-3-ol

Example 45 provides synthesis of a compound shown in Formula Ia, wherein $R_1$=$R_3$=$R_5$=H, $R_2$=methyl, $R_4$-ethyl, and $R_6$-cyclohexyl.

The same synthesis protocol as detailed in Example 6 was followed, by substituting 4-cyclohexylbut-3-en-2-one for 4-(cyclohex-3-en-1-yl) but-3-en-2-one. 1-cyclohexyl-3-methylpent-1-en-3-ol was isolated in 52.1% yield. Odor: pleasant, floral. GC/MS (EI): m/z (%) 182 (1), 164 (8), 153 (17), 135 (20), 121 (3), 107 (11), 99 (5), 93 (22), 85 (8), 79 (26), 71 (100), 67 (38), 55 (35), 41 (50).

EXAMPLE 46: Synthesis of 1-cyclohexyl-3,4-dimethylpent-1-en-3-ol

Example 46 provides synthesis of a compound shown in Formula Ia, wherein $R_1$=$R_3$=$R_5$=H, $R_2$=methyl, $R_4$-isopropyl, and $R_6$=cyclohexyl.

The same synthesis protocol as detailed in Example 8 was followed, by substituting 4-cyclohexylbut-3-en-2-one for 4-(cyclohex-3-en-1-yl) but-3-en-2-one. 1-cyclohexyl-3,4-dimethylpent-1-en-3-ol was isolated in 50.0% yield. Odor: floral, weak. GC/MS (EI): m/z (%) 178 (M$^+$-18, 4), 163 (3), 153 (10), 135 (10), 121 (3), 115 (1), 107 (10), 91 (20), 79 (24), 71 (40), 67 (25), 55 (53), 41 (100).

EXAMPLE 47: Synthesis of 1-cyclohexyl-3-methylhex-1-en-3-ol

Example 47 provides synthesis of a compound shown in Formula Ia, wherein $R_1$=$R_3$=$R_5$=H, $R_2$=methyl, $R_4$-propyl, and $R_6$-cyclohexyl.

The same synthesis protocol as detailed in Example 9 was followed, by substituting 4-cyclohexylbut-3-en-2-one for 4-(cyclohex-3-en-1-yl) but-3-en-2-one. 1-cyclohexyl-3-methylhex-1-en-3-ol was isolated in 33.0% yield. Odor: fatty, aldehydic, floral. GC/MS (EI): m/z (%) 178 (M$^+$-18, 10), 163 (1), 153 (17), 135 (19), 121 (3), 113 (3), 107 (16), 99 (6), 93 (31), 81 (51), 71 (100), 67 (43), 55 (60), 41 (80).

EXAMPLE 48: Synthesis of 4-cyclohexylbut-3-en-2-one oxime

Example 48 provides synthesis of a compound shown in Formula IIa, wherein X=NOH, $R_2$-methyl, $R_3$=$R_5$=H, $R_6$-cyclohexyl.

The same synthesis protocol as detailed in Example 10 was followed, by substituting 4-cyclohexylbut-3-en-2-one for 4-(cyclohex-3-en-1-yl) but-3-en-2-one. 4-cyclohexylbut-3-en-2-one oxime was isolated in 3.2% yield. Odor: harsh, chemical. GC/MS (EI): m/z (%) 167 (6), 150 (1), 136 (1), 122 (1), 108 (3), 98 (1), 94 (6), 84 (61), 79 (12), 71 (2), 67 (27), 55 (98), 41 (100).

EXAMPLE 49: Synthesis of 4-cyclohexylbut-3-en-2-one O-methyl oxime

Example 49 provides synthesis of a compound shown in Formula IIa, wherein X=NOCH$_3$, $R_2$-methyl, $R_3$=$R_5$=H, $R_6$-cyclohexyl.

The same synthesis protocol as detailed in Example 11 was followed, by substituting 4-cyclohexylbut-3-en-2-one for 4-(cyclohex-3-en-1-yl) but-3-en-2-one. 4-cyclohexylbut-3-en-2-one O-methyl oxime was isolated in 50.4% yield. Odor: chemical, weak. GC/MS (EI): m/z(%) 181 (24), 166 (16), 150 (42), 138 (13), 124 (28), 108 (16), 94 (47), 79 (34), 71 (2), 67 (53), 55 (43), 41 (100).

EXAMPLE 50: Synthesis of 3-cyclohexyl-2-methylacrylaldehyde

Example 50 provides synthesis of a compound shown in Formula IIa, wherein X=O, $R_2$=$R_5$=H, $R_3$=methyl, $R_6$=cyclohexyl.

The same synthesis protocol as detailed in Example 12 was followed, by substituting cyclohexanecarbaldehyde for cyclohex-3-ene-1-carbaldehyde. 3-cyclohexyl-2-methylacrylaldehyde was isolated in 42.8% yield. Odor: solventy, paint-like. GC/MS (EI): m/z (%) 152 (49), 137 (9), 123 (13), 109 (28), 95 (43), 81 (64), 67 (100), 55 (42), 41 (83).

EXAMPLE 51: Synthesis of 3-cyclohexyl-2-methylprop-2-en-1-ol

Example 51 provides synthesis of a compound shown in Formula Ia, wherein Rt=$R_2$=$R_4$=$R_5$=H, $R_3$-methyl, and $R_6$-cyclohexyl.

The same synthesis protocol as detailed in Example 13 was followed, by substituting 3-cyclohexyl-2-methylacrylaldehyde for 3-(cyclohex-3-en-1-yl)-2-methylacrylaldehyde. 3-cyclohexyl-2-methylprop-2-en-1-ol was isolated in 69.2% yield. Odor: licorice, blueberry, red fruit., floral green, rose. GC/MS (EI): m/z (%) 154 (3), 136 (2), 123 (19), 99 (100), 81 (79), 67 (52), 55 (60), 41 (61).

EXAMPLE 52: Synthesis of 3-cyclohexyl-2-methylallyl acetate

Example 52 provides synthesis of a compound shown in Formula Ia, wherein $R_1$=C(O)$R_7$, $R_2$=$R_4$=$R_5$=H, $R_3$-$R_7$-methyl, $R_6$=cyclohexyl.

The same synthesis protocol as detailed in Example 3 was followed, by substituting 3-cyclohexyl-2-methylprop-2-en-1-ol for 4-(cyclohex-3-en-1-yl) but-3-en-2-ol. 3-cyclohexyl-2-methylallyl acetate was isolated in 68.5% yield. Odor: herbaceous, musty, dill weed. GC/MS (EI): m/z (%) 196 (1), 165 (1), 154 (6), 136 (59), 121 (84), 107 (18), 93 (30), 81 (53), 67 (33), 55 (34), 41 (100).

EXAMPLE 53: Synthesis of 3-(bicyclo[2.2.1]hept-5-en-2-yl)-2-methylacrylaldehyde oxime Example 53 provides synthesis of a compound shown in Formula IIa, wherein X=NOH, $R_2=R_5=H$, $R_3$-methyl, $R_6$=bicyclo[2.2.1]hept-5-enyl.

The same synthesis protocol as detailed in Example 10 was followed, by substituting 3-(bicyclo[2.2.1]hept-5-en-2-yl)-2-methylacrylaldehyde for 4-(cyclohex-3-en-1-yl) but-3-en-2-one. 3-(bicyclo[2.2.1]hept-5-en-2-yl)-2-methylacrylaldehyde oxime was isolated in 54.4% yield. Odor: earthy, soil, dirt, fruity.

EXAMPLE 54: Synthesis of 3-(bicyclo[2.2.1]hept-5-en-2-yl)-2-methylacrylonitrile Example 54 provides synthesis of a compound shown in Formula IIIa, wherein $R_3$=methyl, $R_5$=H, and $R_6$=bicyclo[2.2.1]hept-5-enyl.

The same synthesis protocol as detailed in Example 22 was followed, by substituting 3-(bicyclo[2.2.1]hept-5-en-2-yl)-2-methylacrylaldehyde oxime for 3-(cyclohex-3-en-1-yl)-2-methylacrylaldehyde oxime. 3-(bicyclo[2.2.1]hept-5-en-2-yl)-2-methylacrylonitrile was isolated in 6.8% yield. Odor: solventy, banana, citrus, green, floral, sour. GC/MS (EI): m/z (%) 159 (11), 144 (15), 131 (10), 117 (32), 105 (18), 91 (21), 77 (15), 66 (100), 51 (17), 39 (40).

EXAMPLE 55: Synthesis of 3-cyclohexyl-2-methylacrylaldehyde oxime

Example 55 provides synthesis of a compound shown in Formula IIa, wherein X=NOH, $R_2=R_5=H$, $R_3$ methyl, $R_6$=cyclohexyl.

The same synthesis protocol as detailed in Example 10 was followed, by substituting 3-cyclohexyl-2-methylacrylaldehyde for 4-(cyclohex-3-en-1-yl) but-3-en-2-one. 3-cyclohexyl-2-methylacrylaldehyde oxime was isolated in 72.1% yield. Odor: green, musty, vegetable. GC/MS (EI): m/z (%) 167 (68), 150 (100), 135 (6), 124 (75), 110 (72), 94 (53), 81 (34), 67 (70), 55 (37), 41 (78).

EXAMPLE 56: Synthesis of 3-cyclohexyl-2-methylacrylonitrile

Example 56 provides synthesis of a compound shown in Formula IIIa, wherein $R_3$-methyl, $R_5$=H, and $R_6$=cyclohexyl.

The same synthesis protocol as detailed in Example 22 was followed, by substituting 3-cyclohexyl-2-methylacrylaldehyde oxime for 3-(cyclohex-3-en-1-yl)-2-methylacrylaldehyde oxime. 3-cyclohexyl-2-methylacrylonitrile was isolated in 57.7% yield. Odor: Sweet, plum, licorice, herbal. GC/MS (EI): m/z (%) 149 (4), 134 (5), 120 (5), 106 (10), 93 (11), 82 (49), 67 (100), 54 (23), 41 (42).

EXAMPLE 57: Fragrance Composition for use in a Liquid Detergent

A ginger mangosteen fragrance composition was prepared using the compound of Example 3 to demonstrate in a liquid detergent. The compound of Example 3 was used as a 10% dilution in DPG. The composition is provided in Table 1.

TABLE 1

| FRAGRANCE CATEGORY | PARTS PER THOUSAND | Wt. % |
|---|---|---|
| Compound of Example 3 (10% in DPG) | 10.0 | 1.0 |
| Citrus | 140.0 | 14.0 |
| Floral | 367.8 | 36.8 |
| Fruity | 169.0 | 16.9 |
| Gourmand | 1.0 | 0.1 |
| Green | 24.0 | 2.4 |
| Herbal | 4.0 | 0.4 |
| Musk | 44.2 | 4.4 |
| Woody and/or amber | 160.0 | 16.0 |
| Solvent (DPG) | 80.0 | 8.0 |
| TOTAL | 1000 | 100 |

A comparative fragrance composition was prepared wherein the compound of Example 3 was replaced with DPG. The comparative fragrance composition is provided in Table 2.

TABLE 2

| FRAGRANCE CATEGORY | PARTS PER THOUSAND | Wt. % |
|---|---|---|
| Citrus | 140.0 | 14.0 |
| Floral | 367.8 | 36.8 |
| Fruity | 169.0 | 16.9 |
| Gourmand | 1.0 | 0.1 |
| Green | 24.0 | 2.4 |
| Herbal | 4.0 | 0.4 |
| Musk | 44.2 | 4.4 |
| Woody and/or amber | 160.0 | 16.0 |
| Solvent (DPG) | 90.0 | 9.0 |
| TOTAL | 1000 | 100 |

A second comparative fragrance composition was prepared with trans-2-dodecenal (@10% in TEC) replacing the compound of Example 3. The second comparative fragrance composition is provided In Table 3.

TABLE 3

| FRAGRANCE CATEGORY | PARTS PER THOUSAND | Wt. % |
|---|---|---|
| Trans-2-dodecenal (10% in TEC) | 10.0 | 1.0 |
| Citrus | 140.0 | 14.0 |
| Floral | 367.8 | 36.8 |
| Fruity | 169.0 | 16.9 |
| Gourmand | 1.0 | 0.1 |
| Green | 24.0 | 2.4 |
| Herbal | 4.0 | 0.4 |
| Musk | 44.2 | 4.4 |
| Woody and/or amber | 160.0 | 16.0 |
| Solvent (DPG) | 80.0 | 8.0 |
| TOTAL | 1000 | 100 |

Each of the fragrance compositions was dosed at 0.7% in a commercial liquid detergent base and evaluated by 5 experts in the field of fragrance evaluation. The composition using the compound of Example 3 was juicier, zestier and less fatty than the composition containing trans-2-dodecenal, and was more powerful, with sparkling citrus notes, compared to the version with DPG.

EXAMPLE 58: Fragrance Composition for use in a Shampoo

A citrus type fragrance composition was prepared from the compound of Example 3 to demonstrate in a shampoo. The compound of Example 3 was used as a 10% dilution in DPG. The fragrance composition is provided in Table 4.

TABLE 4

| FRAGRANCE CATEGORY | PARTS PER THOUSAND | Wt. % |
| --- | --- | --- |
| Compound of Example 3 (10% in DPG) | 100 | 10 |
| Aldehydic | 37 | 3.7 |
| Citrus | 353 | 35.3 |
| Floral | 250 | 25.0 |
| Fruity | 4 | 0.4 |
| Green | 8 | 0.8 |
| Herbal | 46 | 4.6 |
| Musk | 60 | 6.0 |
| Piney | 2 | 0.2 |
| Solvent (DPG) | 140 | 14 |
| TOTAL | 1000 | 100 |

A comparative fragrance composition was prepared wherein the compound of Example 3 was replaced with DPG. The comparative fragrance composition is provided in Table 5.

TABLE 5

| FRAGRANCE CATEGORY | PARTS PER THOUSAND | Wt. % |
| --- | --- | --- |
| Aldehydic | 37 | 3.7 |
| Citrus | 353 | 35.3 |
| Floral | 250 | 25.0 |
| Fruity | 4 | 0.4 |
| Green | 8 | 0.8 |
| Gerbal | 46 | 4.6 |
| Musk | 60 | 6.0 |
| Piney | 2 | 0.2 |
| Solvent (DPG) | 240 | 24 |
| TOTAL | 1000 | 100 |

A second comparative fragrance composition was prepared with trans-2-dodecenal (@10% in DPG) replacing the compound of Example 3. The second comparative fragrance composition is provided in Table 6.

TABLE 6

| FRAGRANCE CATEGORY | PARTS PER THOUSAND | Wt. % |
| --- | --- | --- |
| Trans-2-dodecenal (10% in DPG) | 100 | 10 |
| Aldehydic | 37 | 3.7 |
| Citrus | 353 | 35.3 |
| Floral | 250 | 25.0 |
| Fruity | 4 | 0.4 |
| Green | 8 | 0.8 |
| Herbal | 46 | 4.6 |
| Musk | 60 | 6.0 |
| Piney | 2 | 0.2 |
| Solvent (DPG) | 140 | 14 |
| TOTAL | 1000 | 100 |

Each of the fragrance compositions was dosed at 0.8% in a commercial shampoo base and evaluated by 5 experts in the field of fragrance evaluation. The composition using the compound of Example 3, gave cleaner and more complex citrus notes compared to the version with trans-2-dodecenal, and added greater volume and citrus sparkle compared to the version with DPG.

EXAMPLE 59: Fragrance Composition for use in a Shampoo

A passion fruit type fragrance composition was prepared from the compound of Example 3 to demonstrate in a shampoo. The compound of Example 3 was used as a 10% dilution in DPG. The fragrance composition is provided in Table 7.

TABLE 7

| FRAGRANCE CATEGORY | PARTS PER THOUSAND | Wt. % |
| --- | --- | --- |
| Compound of Example 3 (10% in DPG) | 100.0 | 10 |
| Citrus | 121.0 | 12.1 |
| Floral | 283.0 | 28.3 |
| Fruity | 384.0 | 38.4 |
| Gourmand | 5.0 | 0.5 |
| Green | 21.5 | 2.1 |
| Musk | 35.0 | 3.5 |
| Woody and/or amber | 0.5 | 0.1 |
| Solvent (DPG) | 50 | 5.0 |
| TOTAL | 1000 | 100 |

A comparative fragrance composition was prepared wherein the compound of Example 3 was replaced with DPG. The comparative fragrance composition is provided in Table 8.

TABLE 8

| FRAGRANCE CATEGORY | PARTS PER THOUSAND | Wt. % |
| --- | --- | --- |
| Citrus | 121.0 | 12.1 |
| Floral | 283.0 | 28.3 |
| Fruity | 384.0 | 38.4 |
| Gourmand | 5.0 | 0.5 |
| Green | 21.5 | 2.1 |
| Musk | 35.0 | 3.5 |
| Woody and/or amber | 0.5 | 0.1 |
| Solvent (DPG) | 150 | 15.0 |
| TOTAL | 1000 | 100 |

A second comparative fragrance composition was prepared with trans-2-dodecenal (@10% in DPG) replacing the compound of Example 3. The second comparative fragrance composition is provided in Table 9.

TABLE 9

| FRAGRANCE CATEGORY | PARTS PER THOUSAND | Wt. % |
| --- | --- | --- |
| Trans-2-dodecenal (10% in DPG) | 100.0 | 10 |
| Citrus | 121.0 | 12.1 |
| Floral | 283.0 | 28.3 |
| Fruity | 384.0 | 38.4 |
| Gourmand | 5.0 | 0.5 |

TABLE 9-continued

| FRAGRANCE CATEGORY | PARTS PER THOUSAND | Wt. % |
|---|---|---|
| Green | 21.5 | 2.1 |
| Musk | 35.0 | 3.5 |
| Woody and/or amber | 0.5 | 0.1 |
| Solvent (DPG) | 50 | 5.0 |
| TOTAL | 1000 | 100 |

Each of the fragrance compositions was dosed at 0.8% in a commercial shampoo base and evaluated by 5 experts in the field of fragrance evaluation. The composition using the compound of Example 3, gave more authentic tropical fruit notes without the fattiness when compared to the version with trans-2-dodecenal, and a more natural passion fruit character compared to the version with DPG.

EXAMPLE 60: Fragrance Composition for use in a Liquid Electric Air Freshener A fragrance composition was prepared using from the compound of Example 17 for use in a liquid electric air freshener. The fragrance composition is provided in Table 10.

TABLE 10

| FRAGRANCE CATEGORY | PARTS PER THOUSAND | Wt. % |
|---|---|---|
| Compound of Example 17 | 20 | 2.0 |
| Citrus | 120 | 12.0 |
| Floral | 301.6 | 30.16 |
| Fruity | 4 | 0.4 |
| Gourmand | 4 | 0.4 |
| Musk | .4 | 0.04 |
| Woody and/or amber | 40 | 4.0 |
| Solvent (DPMA) | 510 | 51.0 |
| TOTAL | 1000 | 100 |

A comparative fragrance composition was prepared wherein the compound of Example 17 was replaced with DPG. The comparative fragrance composition is provided in Table 11.

TABLE 11

| FRAGRANCE CATEGORY | PARTS PER THOUSAND | Wt. % |
|---|---|---|
| Solvent (DPG) | 20 | 2.0 |
| Citrus | 120 | 12.0 |
| Floral | 301.6 | 30.16 |
| Fruity | 4 | 0.4 |
| Gourmand | 4 | 0.4 |
| Musk | .4 | 0.04 |
| Woody and/or amber | 40 | 4.0 |
| Solvent (DPMA) | 510 | 51.0 |
| TOTAL | 1000 | 100 |

The fragrance compositions, with and without the compound of Example 17, were evaluated by 2 experts in the field of fragrance evaluation. The composition comprising compound of Example 17 was found to add a rich complex balsamic, powdery note compared to the composition without the compound of Example 17. Additionally, the compound of Example 17 was found to add a cosmetic volume that fills the room. Weight loss of the fragrance in the liquid electric device was not impacted by incorporation of the compound of Example 17.

EXAMPLE 61: Flavor Composition

A flavor composition was prepared from the compound of Example 3. The flavor composition is provided in Table 12.

TABLE 12

| FLAVOR COMPOUND | Wt. % |
|---|---|
| Compound of Example 3 | 0.010 |
| Propylene Glycol | 98.745 |
| Flavor Actives | 1.245 |
| TOTAL | 100 |

A comparative flavor composition was prepared wherein the compound of Example 3 was replaced with propylene glycol. The comparative fragrance composition is provided in Table 13.

TABLE 13

| FLAVOR COMPOUND | Wt. % |
|---|---|
| Propylene Glycol | 98.755 |
| Flavor Actives | 1.245 |
| TOTAL | 100 |

Flavors were dosed at 0.1% in water with 5.0% sugar, 0.1% citric acid, and evaluated by three expert flavor evaluators. The evaluators determined that the composition comprising compound of Example 3 had more pulp-like and juicy character than the control and was more reminiscent of natural grapefruit.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the device, method, and system of the disclosed subject matter without departing from the spirit or scope of the disclosed subject matter. Thus, it is intended that the disclosed subject matter include modifications and variations that are within the scope of the appended claims and their equivalents.

For any patents, patent applications, publications, product descriptions, and protocols are cited throughout this application, the disclosures of all of which are incorporated herein by reference in their entireties for all purposes.

The invention claimed is:

1. A fragrance or flavor compound represented by Formula Ia:

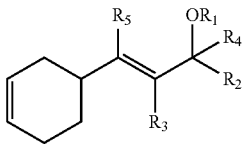

Formula Ia wherein $R_1$ is $C(O)R_7$;
wherein $R_2$ is H or methyl;
wherein $R_3$ is H;
wherein $R_4$ is H, $C_2$-$C_3$ alkyl, or $C_2$-$C_3$ alkenyl;
wherein $R_5$ is H or alkyl; and
wherein $R_7$ is H or methyl.

2. The fragrance or flavor compound of claim 1,
wherein $R_1$ is $C(O)R_7$;
wherein $R_2$ is methyl;
wherein $R_3$ is H;
wherein $R_4$ is H;
wherein $R_5$ is H;
and
wherein $R_7$ is methyl.

3. A fragrance or flavor composition comprising the compound of claim 1.

4. The fragrance composition of claim 3, wherein the concentration of the compound of Formula Ia is from about 0.01% to about 20% by weight of the fragrance composition.

5. The fragrance composition of claim 3, further comprising one or more compounds selected from the group consisting of one or more aldehydic compound(s), one or more animalic compound(s), one or more balsamic compound(s), one or more citrus compound(s), one or more floral compound(s), one or more fruity compound(s), one or more gourmand compound(s), one or more green compound(s), one or more herbaceous compound(s), one or more marine compound(s), one or more mossy compound(s), one or more musk compound(s), one or more piney compound(s), one or more powdery compound(s), one or more spicy compound(s), one or more woody and/or amber compound(s), and combinations thereof.

6. The flavor composition of claim 3, wherein the concentration of the compound of Formula Ia is from about 0.001% to about 20% by weight of the flavor composition.

7. The flavor composition of claim 6, further comprising a flavor carrier.

8. A consumer product comprising the compound of claim 1.

9. A consumer product comprising the composition of claim 3.

* * * * *